United States Patent [19]
Brenner et al.

[11] Patent Number: 5,693,812
[45] Date of Patent: Dec. 2, 1997

[54] POLYMORPHIC FORMS OF AN ANGIOTENSIN II ANTAGONIST

[75] Inventors: Gerald S. Brenner, Norristown, Pa.; Louis S. Crocker, Belle Mead, N.J.; Hossain Jahansouz, North Wales, Pa.; Robert D. Larsen, Bridgewater, N.J.; Chris H. Senanayake, North Brunswick, N.J.; Andrew S. Thompson, Mountainside, N.J.; Karen C. Thompson, Lansdale, Pa.; Thomas R. Verhoeven, Cranford, N.J.

[73] Assignee: Merck & Co. Inc., Rahway, N.J.

[21] Appl. No.: 684,125

[22] Filed: Jun. 3, 1996

[51] Int. Cl.$^6$ .................................................. C07D 491/02
[52] U.S. Cl. ................................................................ 546/118
[58] Field of Search ...................................................... 546/118

[56] References Cited

U.S. PATENT DOCUMENTS 5,332,744  7/1994  Chakravarty et al. ............... 514/261
5,468,764  11/1995  Heitsch et al. ........................ 514/382

*Primary Examiner*—Matthew V. Grumbling
*Assistant Examiner*—Michael Bucknum
*Attorney, Agent, or Firm*—Valerie J. Camara; Mark R. Daniel

[57] ABSTRACT

Polymorphic forms of the angiotensin II receptor antagonist, 3-[2'-(N-benzoyl)sulfonamidobiphenyl-4-yl]methyl-5,7-dimethyl-2-ethyl-3H-imidazo[4,5-b]pyridine and a method for the preparation of these crystal forms.

22 Claims, 15 Drawing Sheets

FORM A (I); FORM B (III); FORM E (II); FORM C (IV)

FIG. 2 FORM D

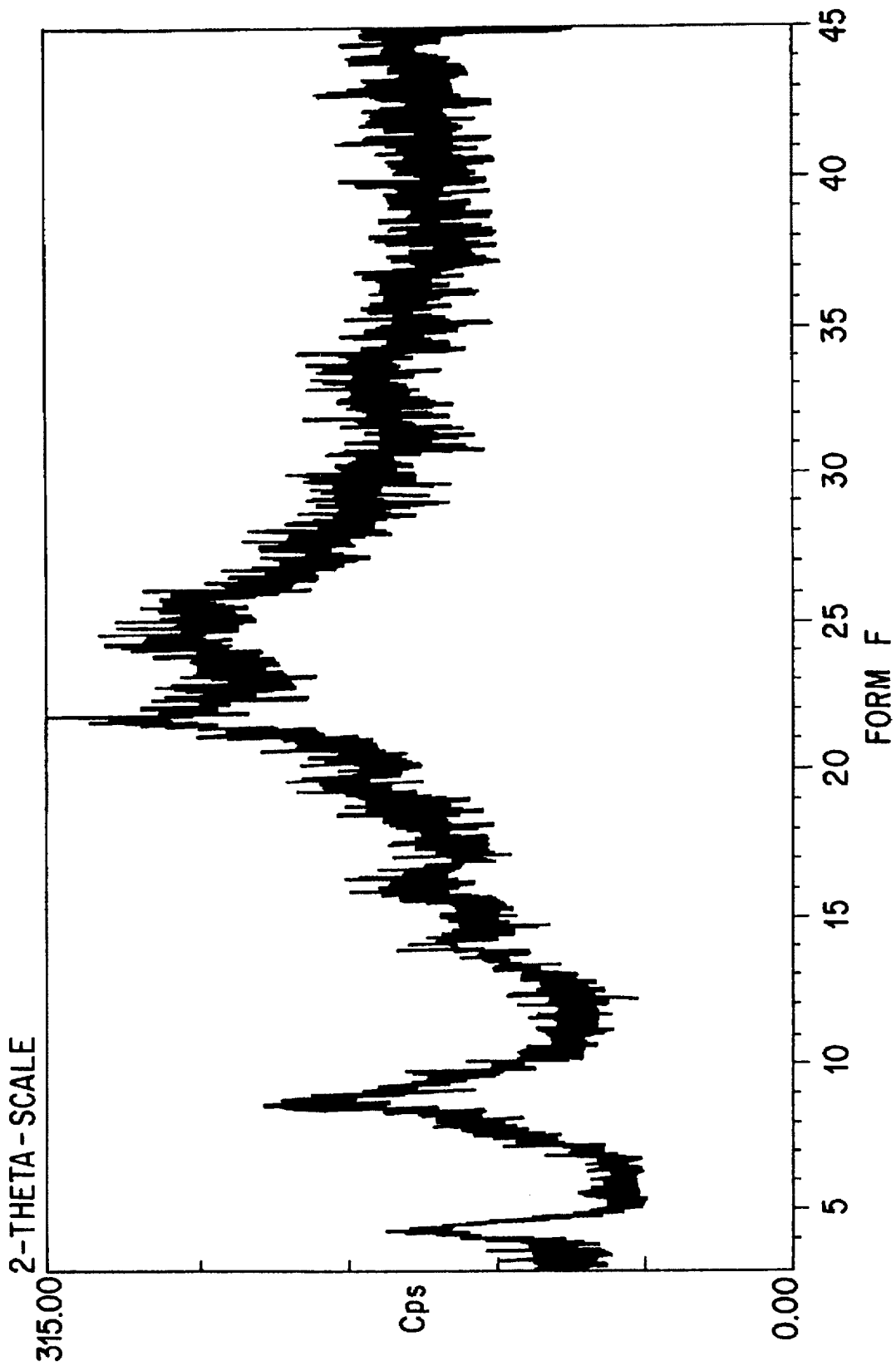
FIG. 15 FORM F

POLYMORPHIC FORMS OF AN ANGIOTENSIN II ANTAGONIST

SUMMARY OF THE INVENTION

This invention relates to a series of polymorphic forms of the angiotensin II receptor antagonist:

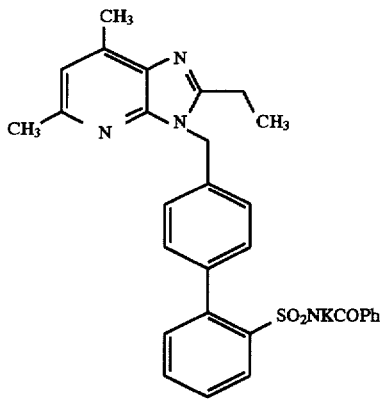

and a method for the preparation of these crystal forms. 3-[2'-(N-benzoyl)sulfonamidobiphenyl-4-yl]methyl-5,7-dimethyl-2-ethyl-3H-imidazo[4,5-b]pyridine potassium salt is disclosed and claimed in U.S. Pat. No. 5,332,744 which issued on Jul. 26, 1994.

The instant invention addresses the need to identify stable crystal forms of this angiotensin II antagonist. The instant invention identifies a series of different crystal forms which each have different stability, solubility and reproducibility chacracteristics.

BACKGROUND OF THE INVENTION

The renin-angiotensin system (RAS) is one of the most important regulators of blood pressure. A decapeptide angiotensen I (AI) is produced from the cleavage of angiotensinogen by the enzyme renin. Angiotensin converting enzyme (ACE) then produces an octapeptide angiotensin II (AII) from AI. ACE also cleaves the nonapeptide bradykinin into inactive fragments.

Blockage of the RAS by ACE inhibitors like captopril and enalapril is one of the most successful ways to treat hypertension and congestive heart failure (CHF). [1] M. A. Ondetti, A. Rubin and D. W. Cushman. Science 196, 441–444 (1977). 2) A. A. Patchett, E. Harris, E. W. Tristram, M. J. Wyvratt, M. T. Wu, D. Taub, E. R. Peterson, T. J. Ikeler, J. ten Broeke, L. G. Payne, D. L. Ondeyka, E. D. Thorsett, W. J. Greenlee, N. S. Lohr, R. D. Hoffsommer, H. Joshua, W. V. Ruyle, J. W. Rothrock, S. D. Aster, A. L. Maycock, F. M. Robinson, R. Hirschmann, C. S. Sweet, E. H. Ulm, D. M. Gross, T. C. Vassil, C. A. Stone. A New Class of Angiotensin Converting Enzyme Inhibitors. Nature 288, 280–283 (1980). 3) P. Corvol, New Therapeutic Prospects of Renin—Angiotensin System Inhibition. Clin. Exp. Hypertens—Theory Practice (Suppl.2) 463–470 (1989).] The ACE inhibitors, also inhibit bradykinin metabolism and cause some side affects like dry cough and angioedema. [4] D. M. Coulter and I. R. Edwards, Brit. Med. J. 294, 1521–1523 (1987).] A series of nonpeptide AII antagonists have recently been developed which are orally active. These compounds block the receptor site of AII without the side-effects associated with ACE inhibitors. [5) Y. Furukawa, S. Kishimoto, K. Nishikawa. Hypotensive Imidazole-5-Acetic Acid Derivatives. U.S. Pat. No. 4,355,040, (1982). 6) A. T. Chiu, J. V. Dunica, D. E. McCall, P. C. Wong, W. A. Price, M. J. M. C. Thoolen, D. J. Carini, A. L. Johnson, P. B. M. W. M. Timmermans. Nonpeptide Angiotensin II Receptor Antagonists. III, Structure-Function Studies. J. Pharmacol. Exp. Ther. 250, 867–874 (1989). 7) P. C. Wong, W. A. Price Jr., A. T. Chiu, N.Y. Wong, J. V. Dunica, D. J. Carini, A. L. Johnson, P. B. M. W. M. Timmermans. EXP-6803, A Nonpeptide Angiotensin II Receptor Antagonist. Cardiovasc. Drug Rev. 7, 285–300 (1989). 8) J. V. Dunica, A. T. Chin, D. J. Carini, G. B. Gregory, A. L. Johnson, W. A. Price, G. J. Wells, P. C. Wong, J. C. Calabrese P. B. M. W. M. Timmermans. The Discovery of Potent Nonpeptide Angiotensin II Receptor Antagonists: A New Class of Potent Antihypertensives. J. Med. Chem. 33, 1312–1329 (1990). 9) P. C. Wong, W. A. Price, A. T. Chiu, D. J. Carini, J. V. Dunica, A. L. Johnson, R. R. Wexler, P. B. M. W. M. Timmermans. Nonpeptide. Angiotensin II receptor Antagonists: Studies with EXP9270 and DUP 753. Hypertension 15, 823–834 (1990). 10) J. V. Duncia, D. J. Carini, A. T. Chiu, A. L. Johnson, W. A. Price, P. C. Wong, R. R. Wexler, P. B. M. W. M. Timmermans, The Discovery of DUP-753 an Orally Active Nonpeptide Angiotensin II Receptor Antagonist, Med. Res.Rev., 12, 149–191 (1992).] Losartan is the first compound in the AII receptor antagonist series to be submitted for regulatory approval. [11) K. Raghavan, A. Dwivedi, G. C. Campbell Jr., E. Johnson, D. Levorse, J. McCauley, M. Hussain. A Spectroscopic Investigation of Losartan Polymorphs. Pharm. Res. 10, 900–904 (1993).] 3-[2'-(N-benzoyl)sulfonamido-biphenyl-4-yl]methyl-5,7-dimethyl-2-ethyl-3H-imidazo[4,5-b]pyridine potassium salt, is similar to losartan and exhibits a high affinity for $AT_1$ receptors and a low affinity for $AT_2$ binding sites.

3-[2'-(N-benzoyl) sulfonamidobiphenyl-4-yl]methyl-5,7-dimethyl-2-ethyl-3H-imidazo[4,5-b]pyridine potassium salt was found to have numerous crystal forms. Recrystallization of the material with different solvents produced new crystal forms. Studies were carried out to characterize these polymorphs and to determine which polymorphic form is thermodynamically most stable, and how the recommended polymorphic form could be reproducibly prepared. X-ray powder differaction (XRPD), solution calorimetry, differential scanning calorimetry (DSC), thermogravimetric analysis (TGA) and solubility data have been widely used to charaterize polymorphs and to identify thermodynamically stable form. [12) D. P. Ip, G. S. Brenner, J. M. Stevenson, S. Lindenbaum, A. W. Douglas, S. D. Klein, and J. A. McCauley. High Resolution Spectroscopic Evidence and Solution Calorimetry Studies on the Polymorphs of Enalapril Maleate. Int. J. Pharm. 28, 183–191 (1986).] Utilizing these techniques, polymorphs of 3-[2'-(N-benzoyl) sulfonamidobiphenyl-4-yl]methyl-5,7-dimethyl-2-ethyl-3H-imidazo[4,5-b]pyridine potassium salt were assessed.

Figure 1:
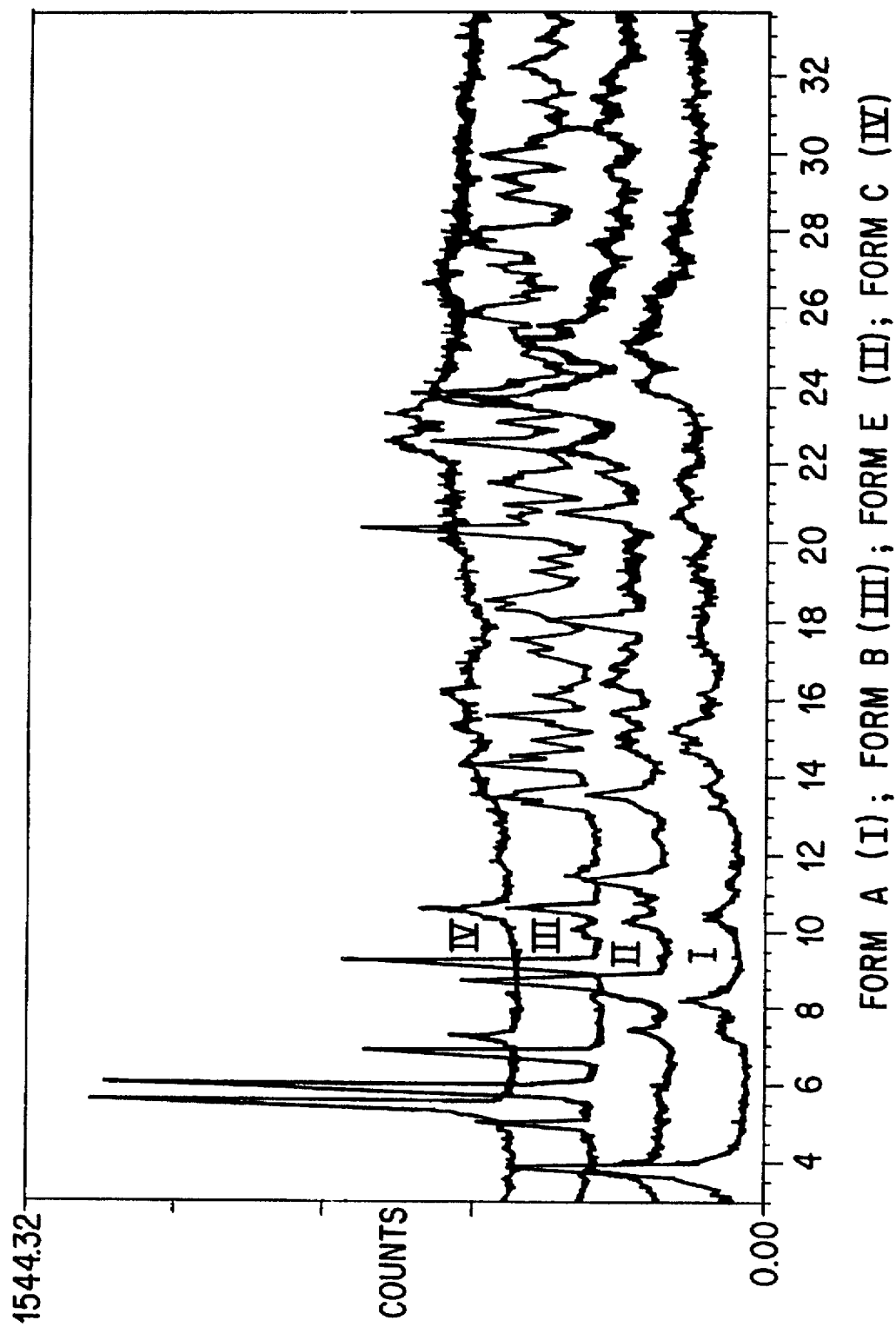
FIG. 1.
Figure 2:
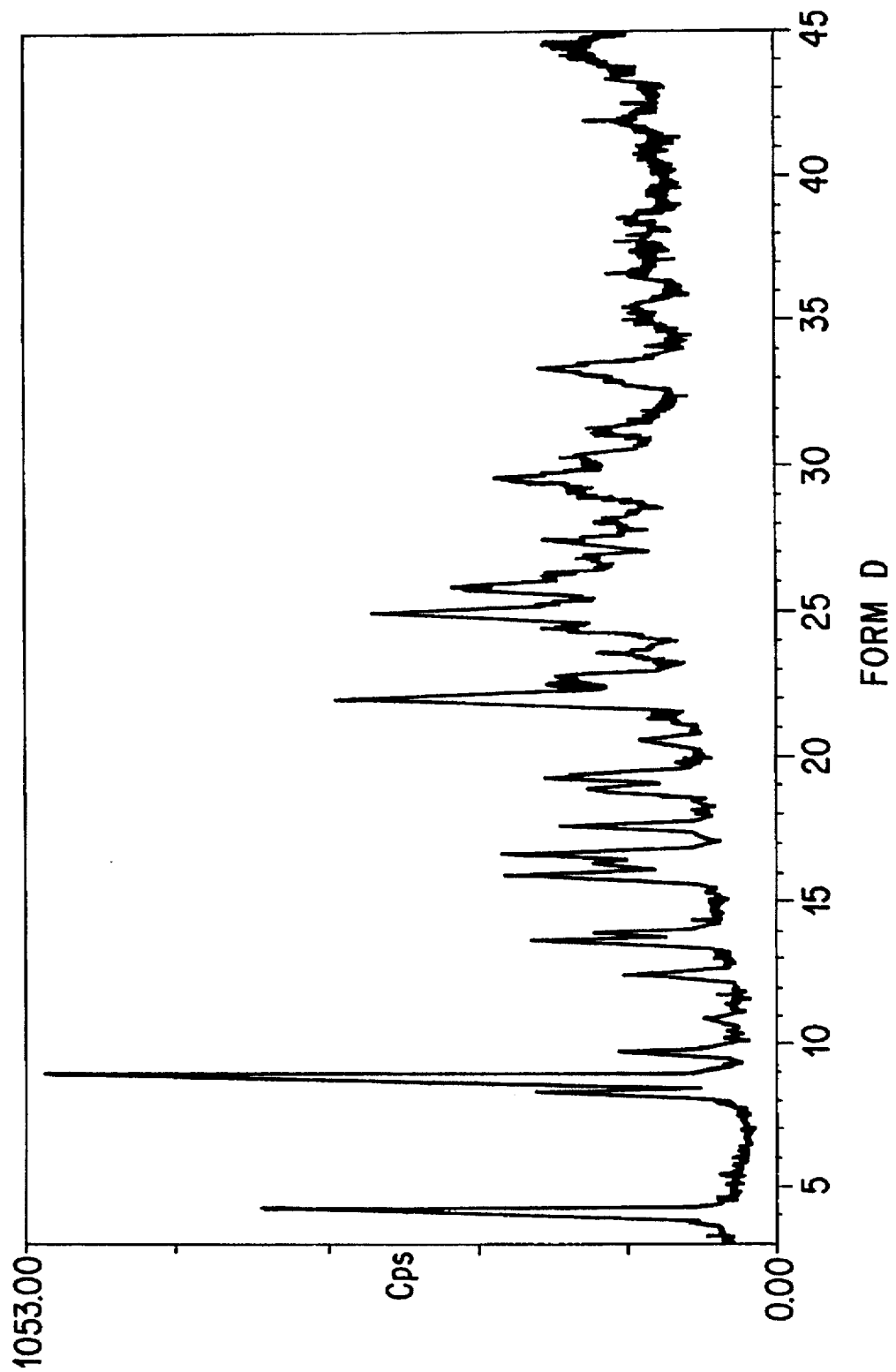

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorphs: (I). Form A; (II). Form E; (III). Form B; and (IV). Form C.

FIG. 2.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form D.

FIG. 3.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form G.

3

FIG. 4.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form I.

FIG. 5.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form $I_d$.

FIG. 6.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form J.

FIG. 7.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form W.

FIG. 8.

Thermogravimetric Analysis weight loss curve of 3-[2'-(N-benzoyl)sulfonamidobiphenyl-4-yl]methyl-5,7-dimethyl-2-ethyl-3H-imidazo[4,5-b]pyridine potassium salt polymorph Form I.

FIG. 9.

Thermogravimetric Analysis weight loss curve of 3-[2'-(N-benzoyl)sulfonamidobiphenyl-4-yl]methyl-5,7-dimethyl-2-ethyl-3H-imidazo[4,5-b]pyridine potassium salt polymorph Form $I_d$.

FIG. 10.

Differential Scanning Calorimetric thermogram of 3-[2'-(N-benzoyl)sulfonamidobiphenyl-4-yl]methyl-5,7-dimethyl-2-ethyl-3H-imidazo[4,5-b]pyridine potassium salt polymorph Form $B_3$, wherein the heating rate was 20° C. per minute.

FIG. 11.

Differential Scanning Calorimetric thermogram of 3-[2'-(N-benzoyl)sulfonamidobiphenyl-4-yl]methyl -5,7-dimethyl-2-ethyl-3H-imidazo[4,5-b]pyridine potassium salt polymorph Form I, wherein the heating rate was 20° C. per minute.

FIG. 12.

Differential Scanning Calorimetric thermogram of 3-[2'-(N-benzoyl)sulfonamidobiphenyl-4-yl]methyl-5,7-dimethyl-2-ethyl-3H-imidazo[4,5-b]pyridine potassium salt polymorph Form $I_d$, wherein the heating rate was 20° C. per minute.

FIG. 13.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form H.

FIG. 14.

Differential Scanning Calorimetric thermogram of 3-[2'-(N-benzoyl)sulfonamidobiphenyl-4-yl]methyl-5,7-dimethyl-2-ethyl-3H-imidazo[4,5-b]pyridine potassium salt polymorph Form H, wherein the heating rate was 20° C. per minute.

FIG. 15.

X-ray powder diffraction pattern of 3-[2'-(N-benzoyl) sulfonamidobiphenyl-4-yl]methyl-5,7-dimethyl-2-ethyl-3H-imidazo[4,5-b]pyridine potassium salt polymorph Form F.

4

DETAILED DESCRIPTION OF THE INVENTION

This invention relates to novel crystal forms of:

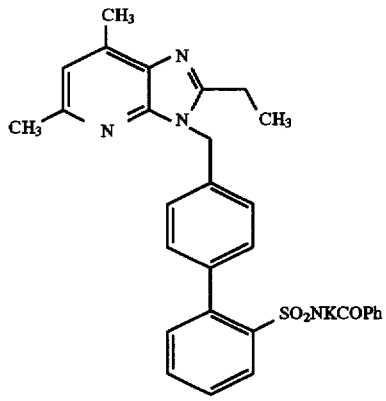

and a process for synthesizing these crystal forms.

Figure 3:
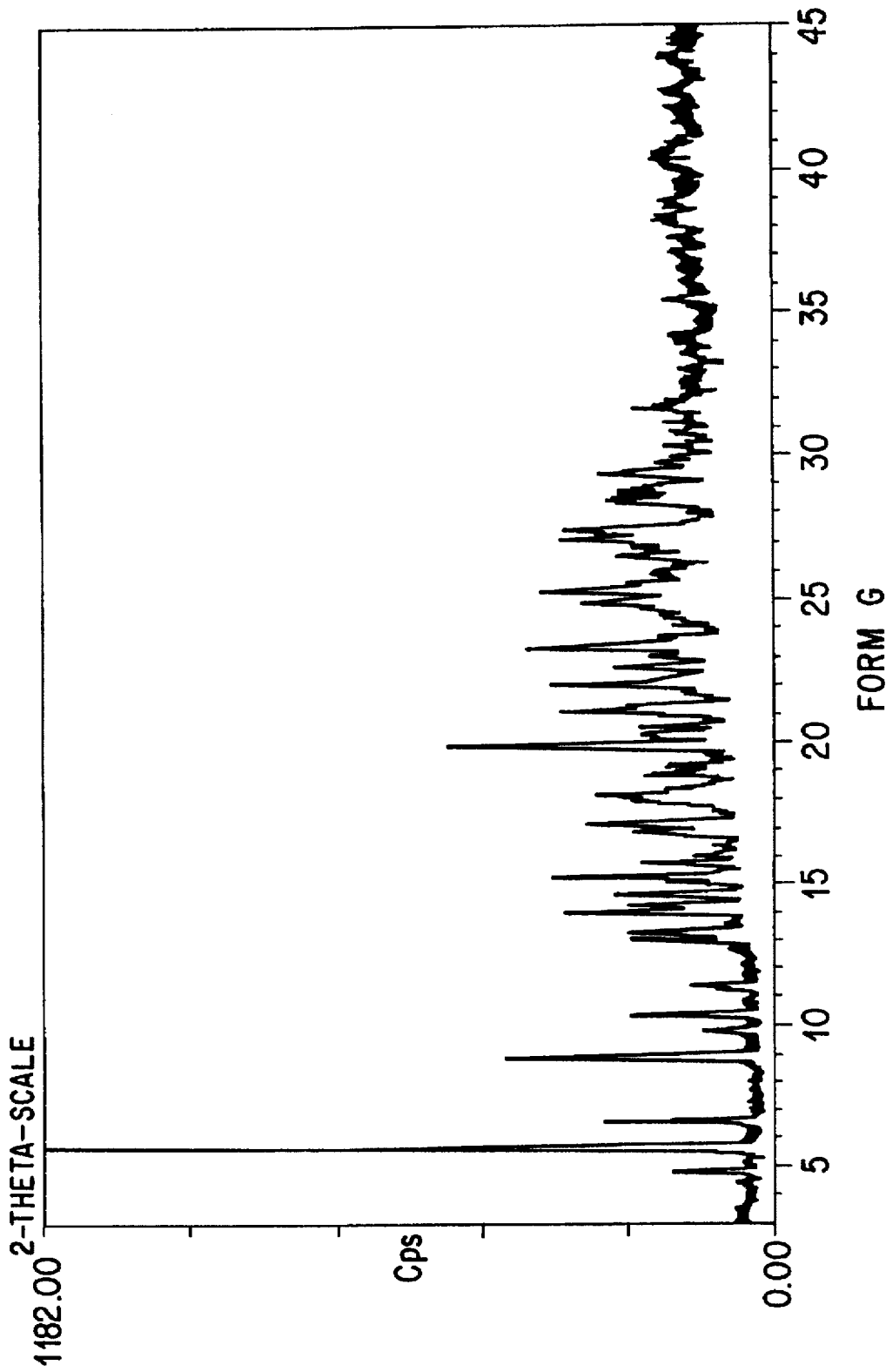

The XRPD patterns of different lots of 3-[2'-(N-benzoyl) sulfonamidobiphenyl-4-yl]methyl-5,7-dimethyl-2-ethyl-3H-imidazo[4,5-b]pyridine potassium salt were different from each other, suggested that their crystal forms were unique. [13] S. R. Byre. "Solid State Chemistry of Drugs." Academic Press, New York, 1982.] FIG. 1 shows XRPD patterns of forms "A", "B", "C", and "E". Recrystallization of any of these lots from solvents like ethanol, methanol, isopropanol, acetone, etc. gave new crystal forms different from the original forms. To determine which polymorph was the most stable and develop methods to reproducibly prepare the polymorph, several experiments were conducted. Solubility in water at room temperature was one of these techniques. The equilibrium solubility in water, at room temperature for five polymorphs (Forms "B", "C", "D", "F", and "G") were the same (Table 1). When the remaining solids were filtered, air dried or vacuum dried overnight at room temperature the XRPD patterns had changed from the initial patterns and all were exactly the same. These experiments indicate that all of the crystal forms converted in water at room temperature to a new crystalline form designated "D". The XRPD pattern of form "D" is shown in FIG. 3. The crystal form "D" after heating at 40° C. for 30 minutes did not change, but when heating was continued for 24 hours crystallinity was reduced and XRPD pattern changed to a new form called "F". Heating of forms "D", "F" or any lot up to 190° C. for just a few minutes produced a new crystalline anhydrous form designated "G". These two new forms ("F" and "G") in water, at room temperature were also converted to form "D". The flow chart below shows the interconversion of the various crystal forms.

TABLE I

Physical Properties of Polymorphs of 3-[2'-(N-benzoyl)sulfonamidobiphenyl-4-yl]methyl-5,7-dimethyl-2-ethyl-3H-imidazo[4,5-b]pyridine potassium salt

| Crystal Form | Solubility in water (mg/ml) | % Weight Loss (Δ 30–150° C. by TGA) | ΔH solution DMSO at 30° C. (J/g) | ΔH solution 88% DMSO/ 12% $H_2O$ (J/g) |
|---|---|---|---|---|
| A | | 3.4 | 4.92 ± 0.47 | |
| B | | 0.5 | 17.78 ± 0.52 | |
| C | | 0.6 | 29.75 ± 0.46 | |

TABLE I-continued

Physical Properties of Polymorphs of 3-[2'-(N-benzoyl)sulfonamido-biphenyl-4-yl]methyl-5,7-dimethyl-2-ethyl-3H-imidazo[4,5-b]pyridine potassium salt

| Crystal Form | Solubility in water (mg/ml) | % Weight Loss (Δ 30–150° C. by TGA) | ΔH solution DMSO at 30° C. (J/g) | ΔH solution 88% DMSO/ 12% H₂O (J/g) |
|---|---|---|---|---|
| D | 10.4 ± 0.7 | 12–14 | −1.36 ± 0.42 | −16.33 ± 1.61 |
| F | | | | |
| G | | 0 | 8.51 ± 0.66 | |
| I | 8.0 ± 0.4 | 4.1–5.9 | −8.56 ± 1.64 | −25.68 ± 2.67 |
| J | | 0.7 | | |

Conversion of Crystal Forms any crystal form of 3-[2'-(N-benzoyl)sulfonamido-biphenyl-4-yl]methyl-5,7-dimethyl-2-ethyl-3H-imidazo[4,5-b]pyridine potassium salt
(Before the discovery of Form "I".)

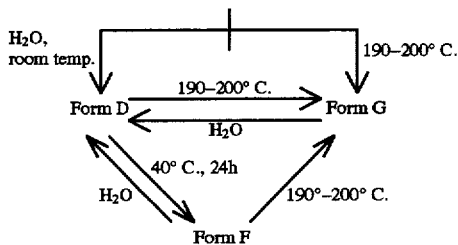

any crystal form of 3-[2'-(N-benzoyl)sulfonamido-piphenyl-4-yl]methyl-5,7-dimethyl-2-ethyl-3H-imidazo[4,5-b]pyridine potassium salt
(After the discovery of Form "I".)

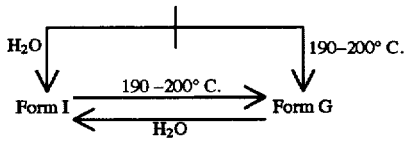

Figure 4:
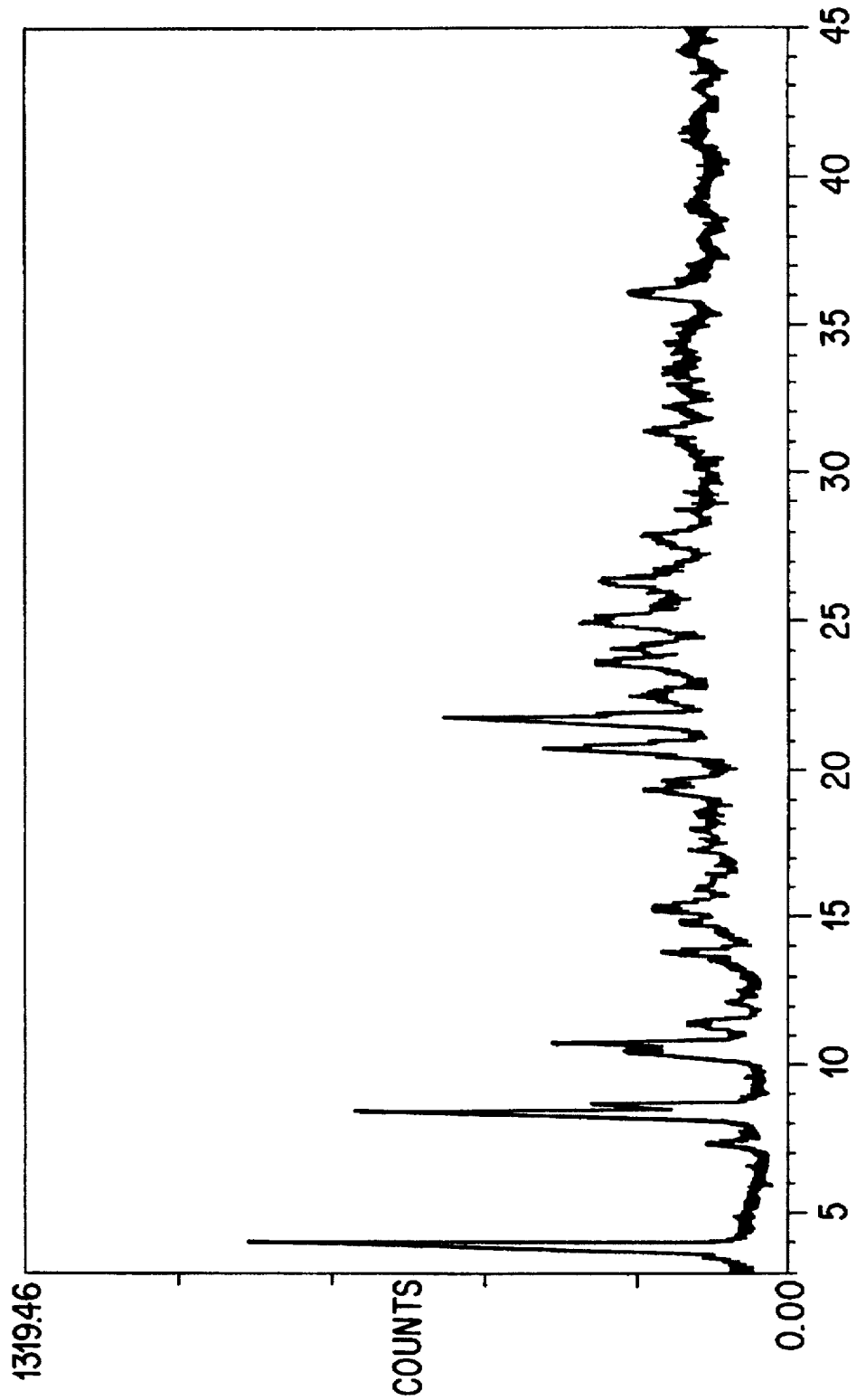

Since all of the crystal forms of 3-[2'-(N-benzoyl) sulfonamidobiphenyl-4-yl]methyl-5,7-dimethyl-2-ethyl-3H-imidazo[4,5-b]pyridine potassium salt were changed to a single crystal form "D", in water, the effect of a non-aqueous solvent was studied. 3-[2'-(N-benzoyl) sulfonamidobiphenyl-4-yl]methyl-5,7-dimethyl-2-ethyl-3H-imidazo[4,5-b]pyridine potassium salt, Forms "A", "B", "C", and "D" were stirred overnight at room temperature in acetonitrile. The remaining solids were filtered and then vacuum dried overnight at room temperature. The crystallinity of the solids was examined by XRPD spectroscopy. Form "A" and form "D" which were initially hydrated (Table I) were converted to a new crystal form ("I") and Forms "B" and "C" which were initially anhydrous were changed to another new form ("J"). The XRPD pattern of form "I" is shown in FIG. 4. Table I shows the percent water of the crystal forms by TGA.

All of the crystal forms were converted to a single crystal form ("D") in water, but in acetonitrile to two different crystal forms. The crystal forms which initially contained some water (forms "A" and "D") were changed to form "I" and the anhydrous crystal forms were converted to form "J". To explore the role of water in the above experiments, 3-[2'-(N-benzoyl)sulfonamidobiphenyl-4-yl]methyl-5,7-dimethyl-2-ethyl-3H-imidazo[4,5-b]pyridine potassium salt, form "C" (an anhydrous crystal form) was this time suspended in acetonitrile with added water (water was 10% of the solid weight). As a control experiment Form "C" was also suspended in acetonitrile with no added water. The samples were shaken overnight at room temperature. The remaining solids were filtered and vacuum dried overnight at room temperature. The XRPD patterns of these two solids indicate that in absence of water form "C" was changed to form "J", but in acetonitrile containing same water it can be converted to form "I". When other crystal forms, including form "D" were also suspended in acetonitrile-water and shaken overnight at room temperature, the final crystal form was also "I".

To find out whether form "I", which was obtained reproducibly, was also the thermodynamically stable crystal form of 3-[2'-(N-benzoyl)sulfonamidobiphenyl-4-yl] methyl-5,7-dimethyl-2-ethyl-3H-imidazo[4,5-b]pyridine potassium salt at room temperature, the equilibrium solubility of form "I" in water, was studied. In contrast to the equilibrium solubility of the other crystal forms in water (10 mg/ml, pH 7.8), the solubility of form "I" under the same experimental conditions was 8.0 mg/ml.

Form I when heated to about 216° C., was converted to form H. Form H was found to have an XRPD pattern characteristic of crystalline material. When form H was analyzed by differential scanning calorimetry, a single endotherm with a peak temperature of 259° C. was observed.

The remaining form "I" solid after equilibrium solubility studies in water was removed by filtration and vacuum dried overnight at room temperature. The XRPD patterns of the solid indicated that in contrast to other crystal forms, form "I" was the only crystal form that in water remained unchanged.

The heat of solution of different crystal forms of 3-[2'-(N-benzoyl)sulfonamidobiphenyl-4-yl]methyl-5,7-dimethyl-2-ethyl-3H-imidazo[4,5-b]pyridine potassium salt were studied at 30° C. The heat of solution is a measure of the crystal lattice energy. This would imply that the sample with the most endothermic heat of solution would be the most stable. The heats of solution which were determined for the various polymorphs of 3-[2'-(N-benzoyl) sulfonamidobiphenyl-4-yl]methyl-5,7-dimethyl-2-ethyl-3H-imidazo[4,5-b]pyridine potassium salt are further complicated because these polymorphs contain varying amounts of water. They are therefore not chemically identical. Heats of solution had to be conducted in a solvent which dissolved the samples quickly without conversion to another polymorph. This really limited solvents which could be used. Dimethylsulfoxide was chosen for this reason. The heats of solution therefore have contributions from the lattice energy of the solid as well as heat of dilution of lattice water in dimethylsulfoxide. The calorimeter therefore produces a complex signal that has an exothermic contribution from the water and an additional contribution from the energy required to dissolve the crystal. The heat of solution data presented in Table I clearly show that Form "I" has the most endothermic heat of solution and therefore would appear to be the most stable. Additional heats of solution were determined in a mixed solvent system of 88% dimethylsulfoxide and 12% water. This system was used to minimize the contribution of moisture to the heat of solution. Again the heat of solution of form "I" is the most endothermic suggesting that it has the greatest thermodynamic stability. Based on these studies, which were in agreement with the equilibrium solubility studies in water, form "I" is the thermodynamically stable crystal form of 3-[2'-(N-benzoyl) sulfonamidobiphenyl-4-yl]methyl-5,7-dimethyl-2-ethyl-3H-imidazo[4,5-b]pyridine potassium salt.

Figure 5:
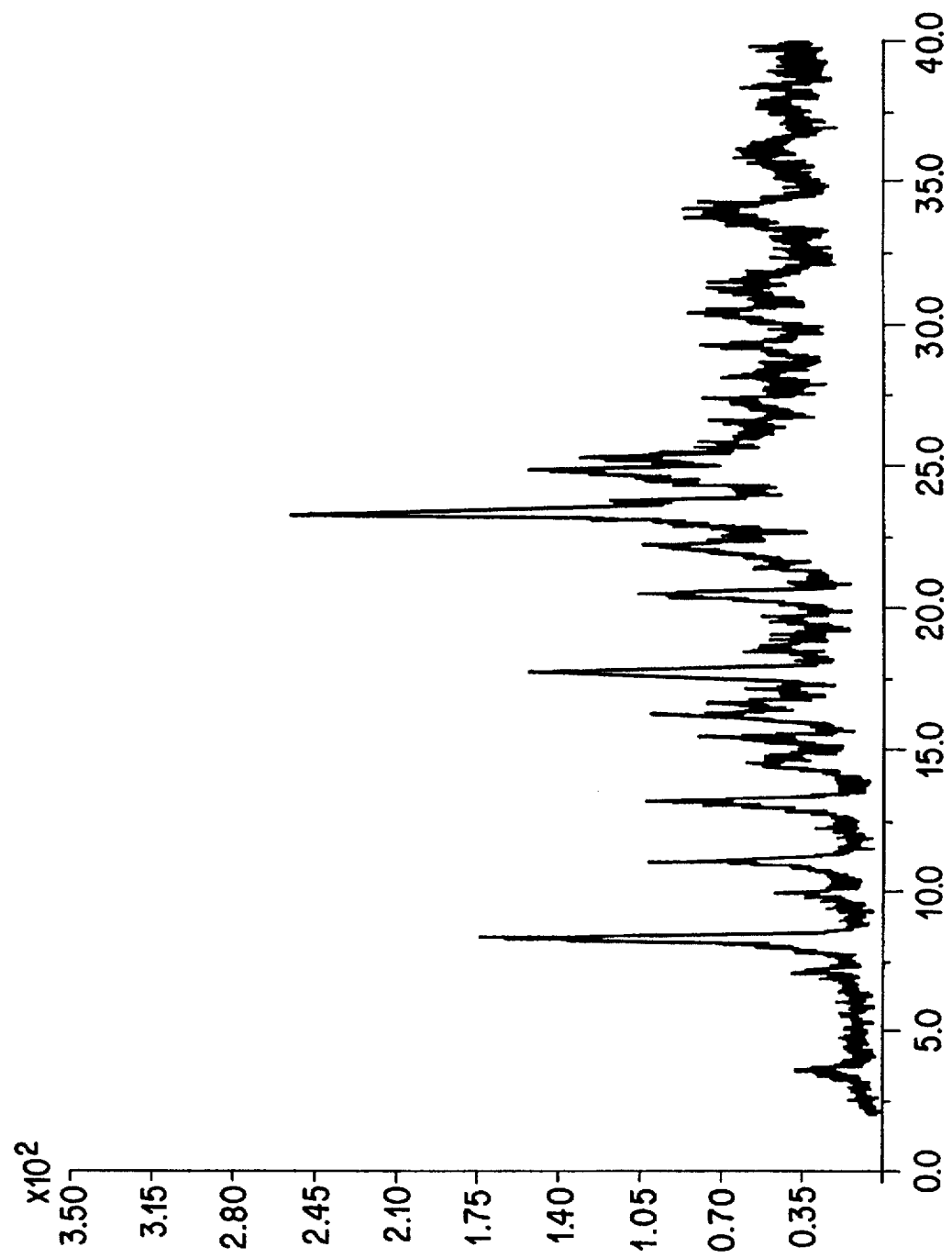
Figure 6:
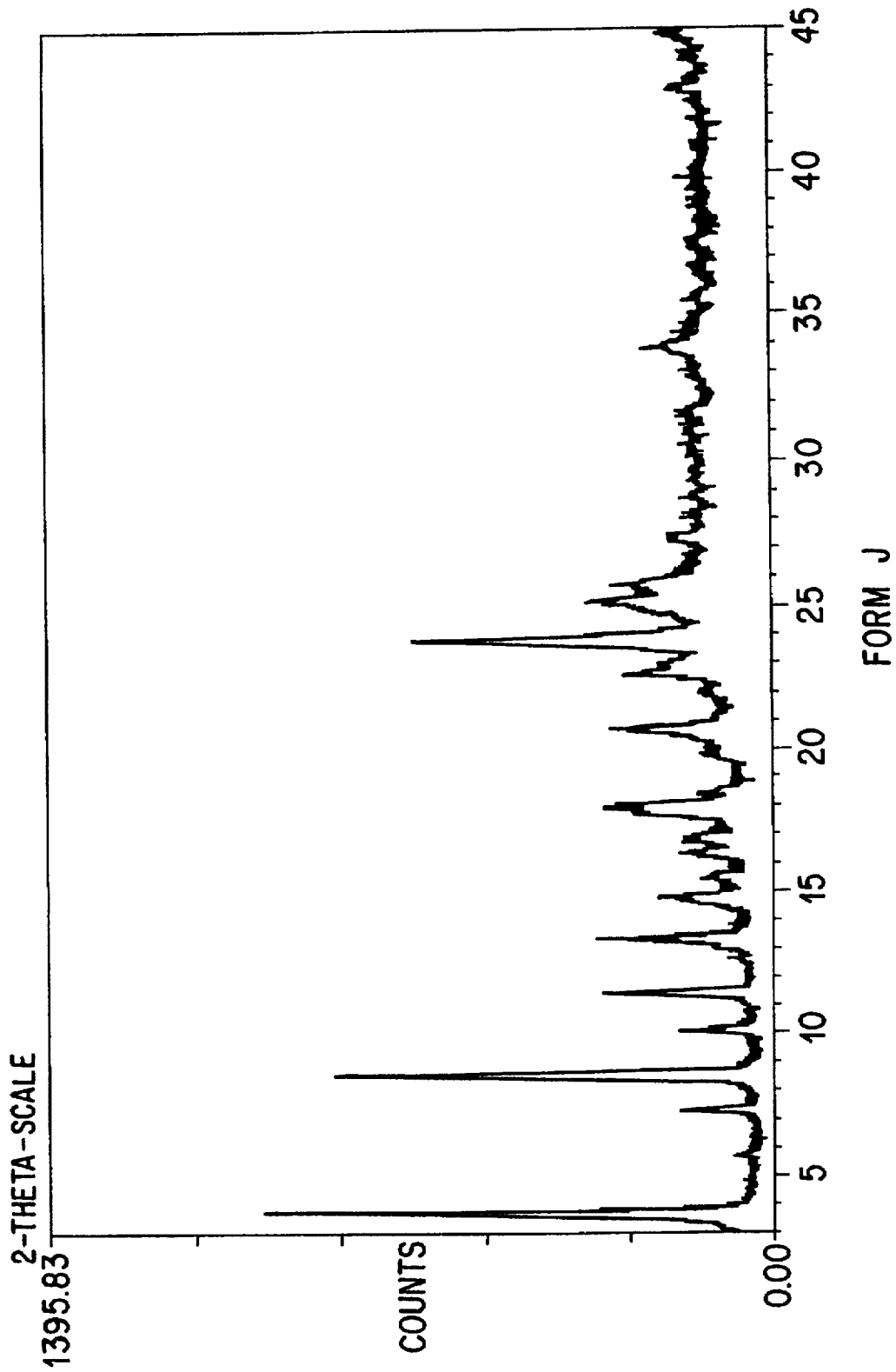
Figure 7:
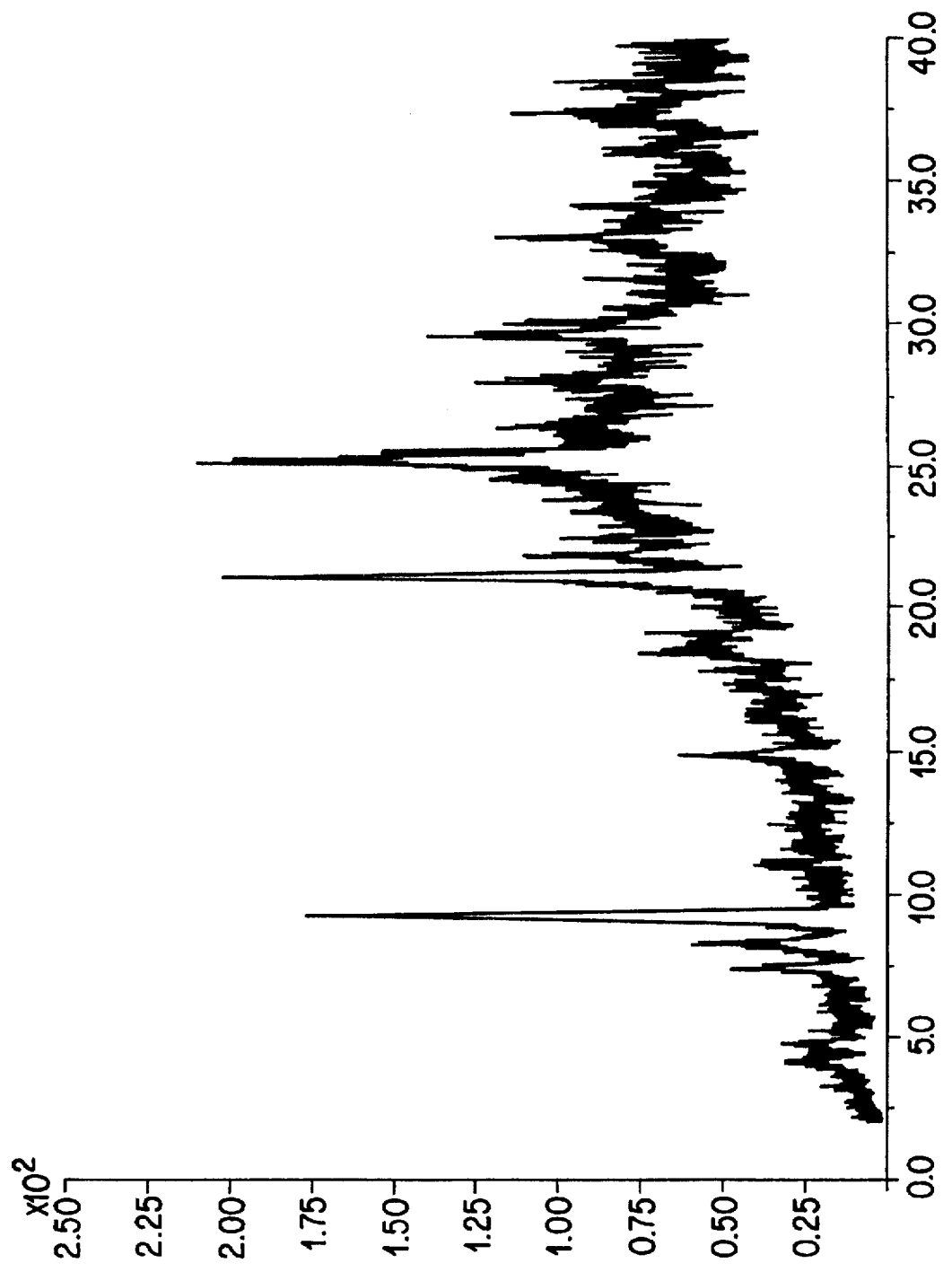
Figure 8:
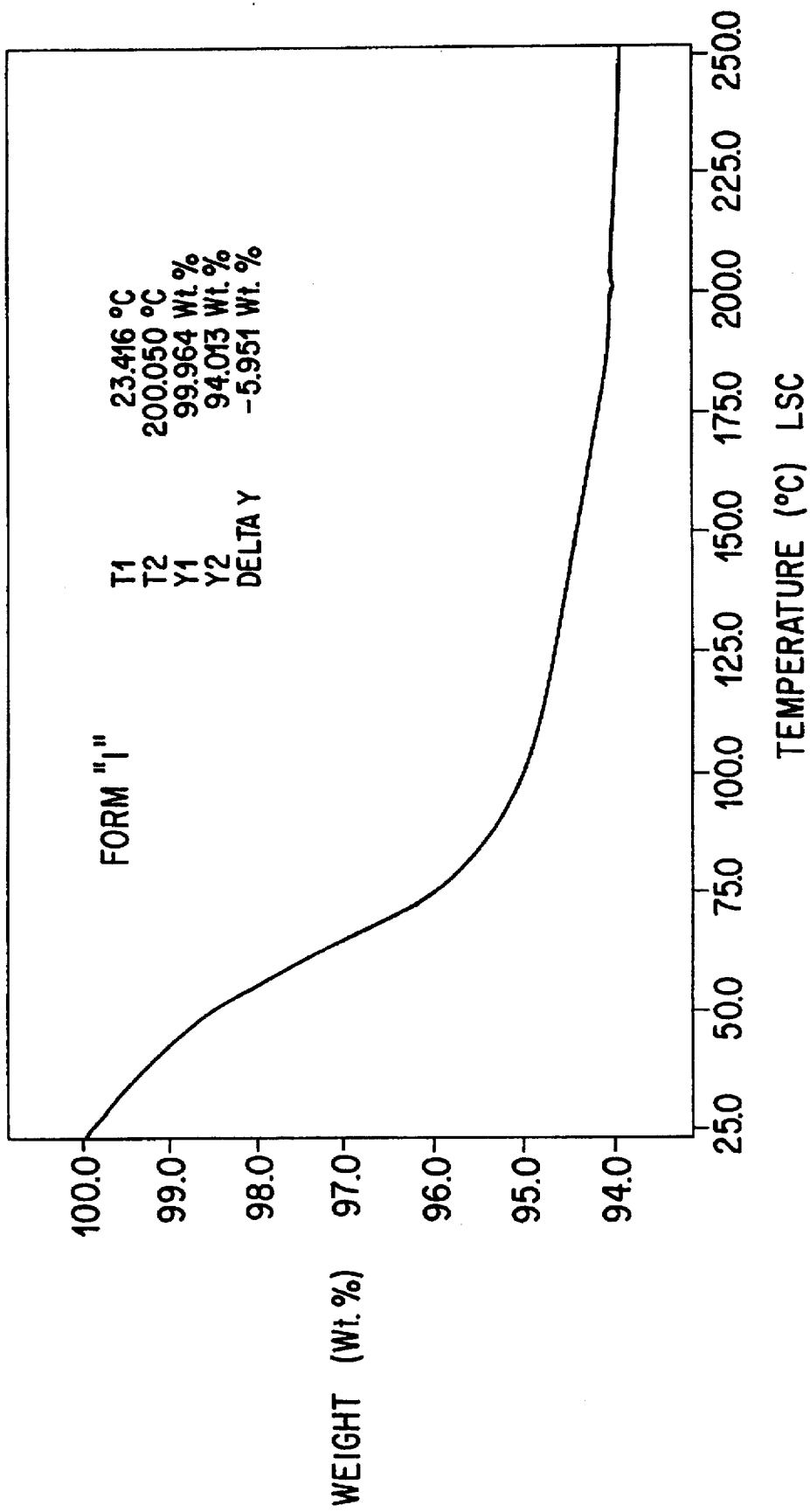
Figure 9:
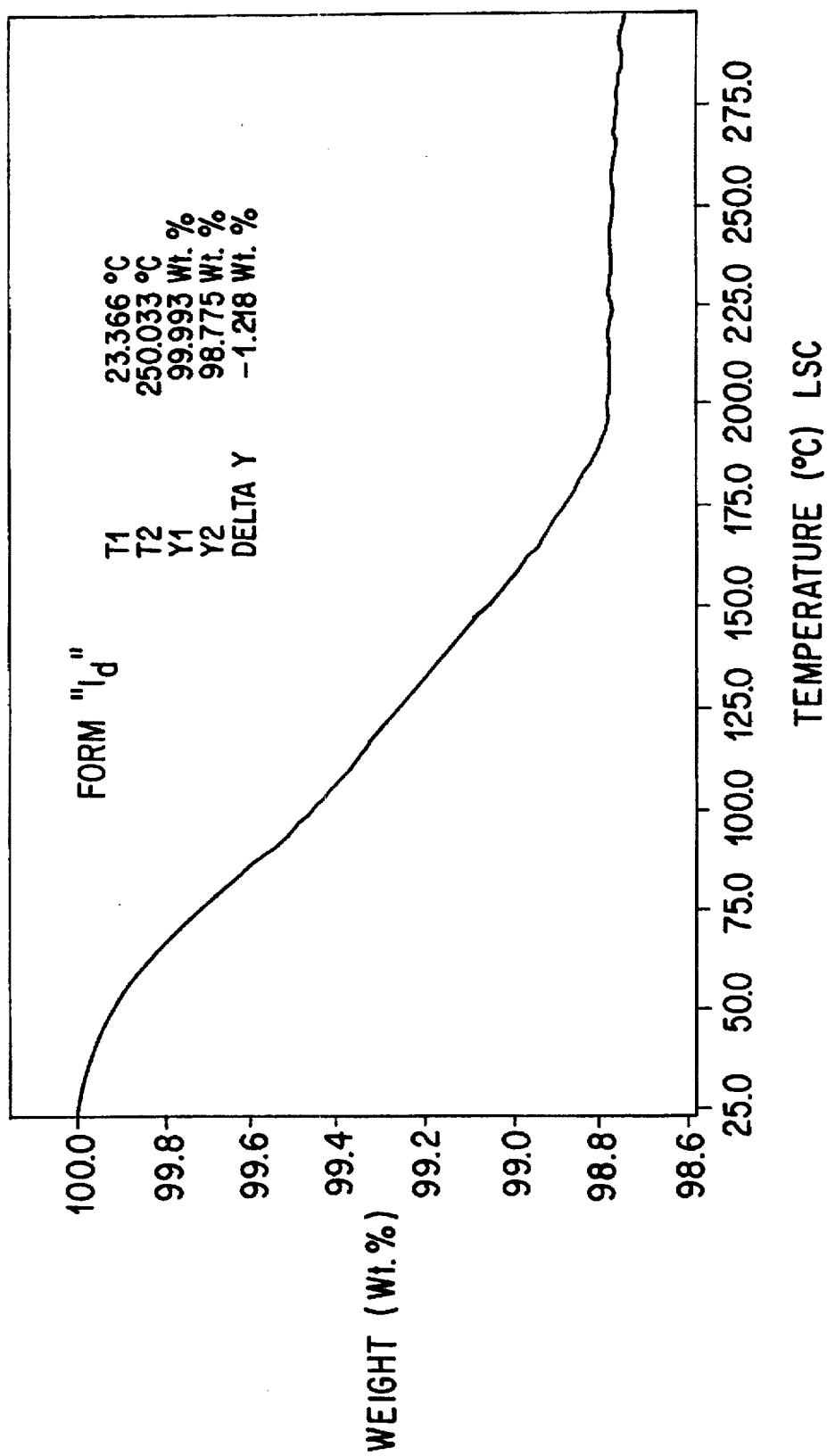
Figure 10:
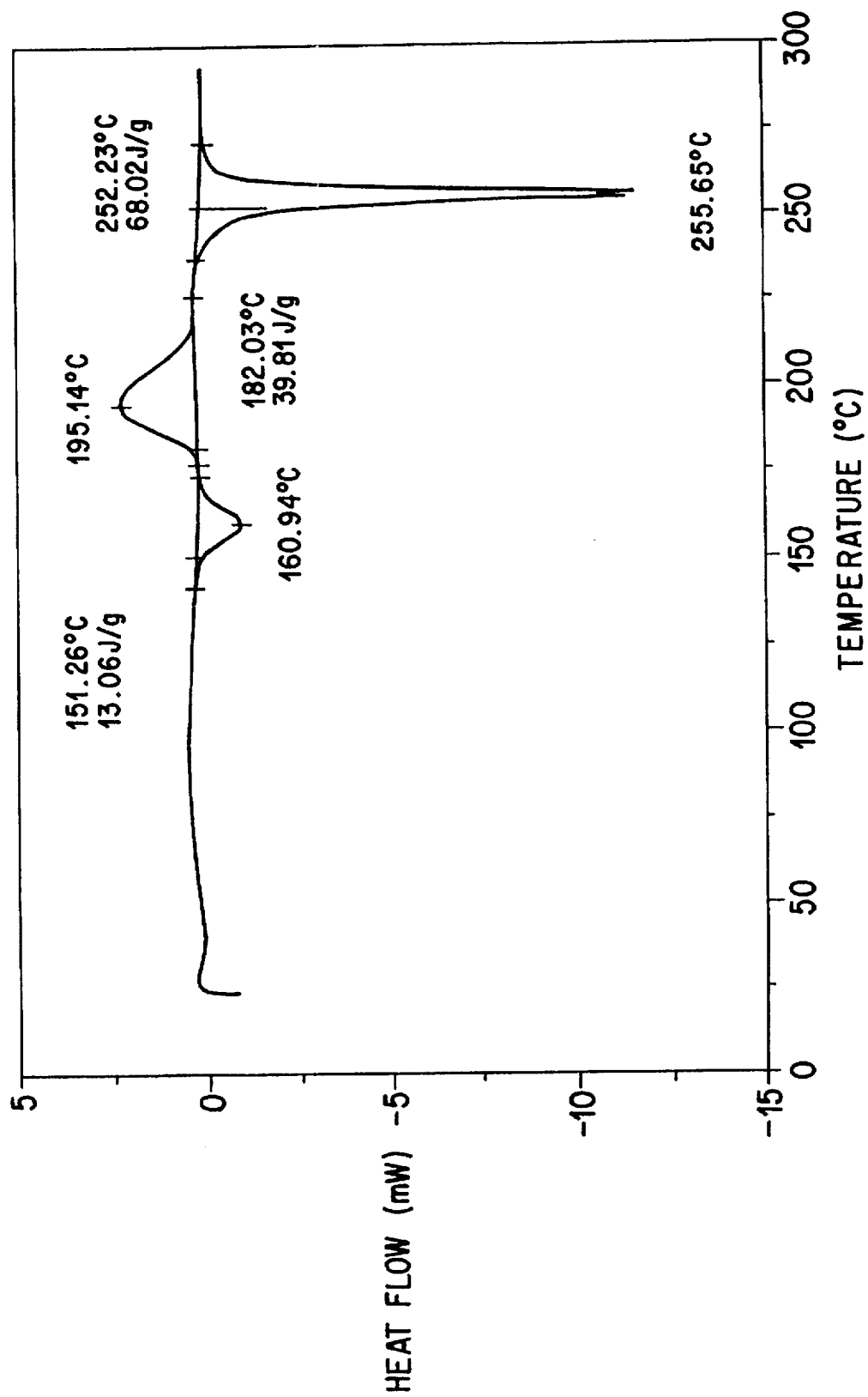
Figure 11:
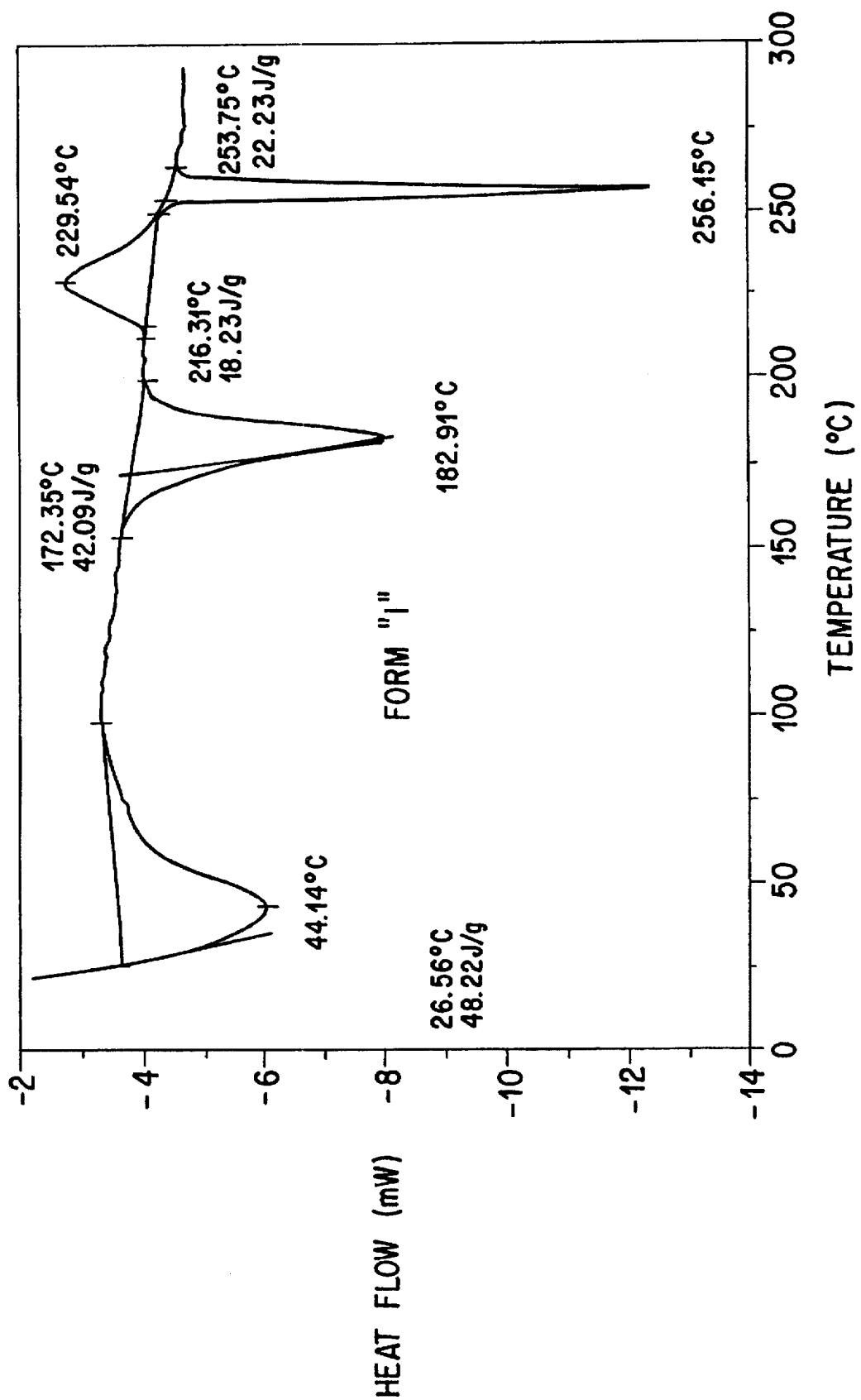
Figure 12:
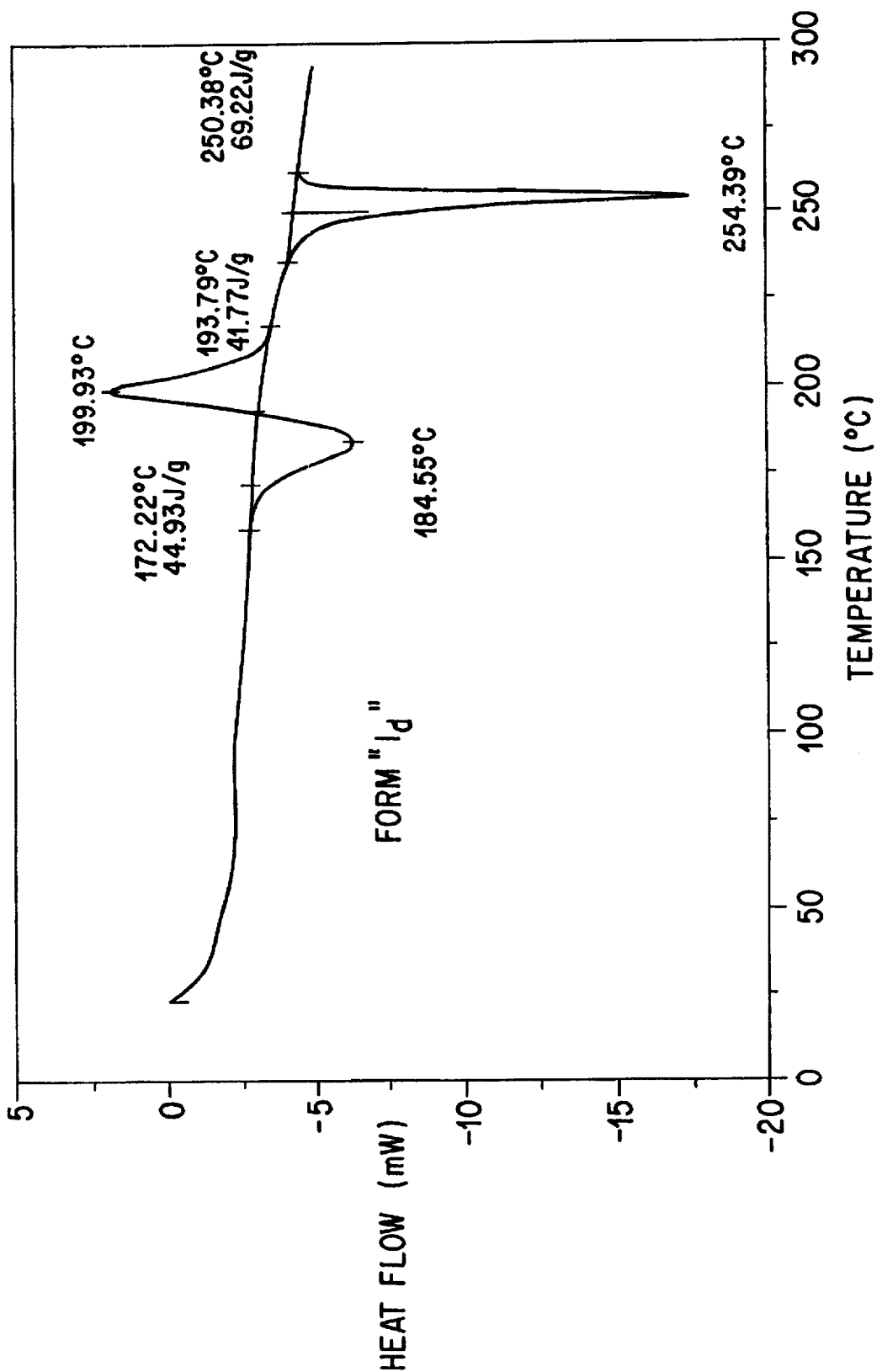
Figure 13:
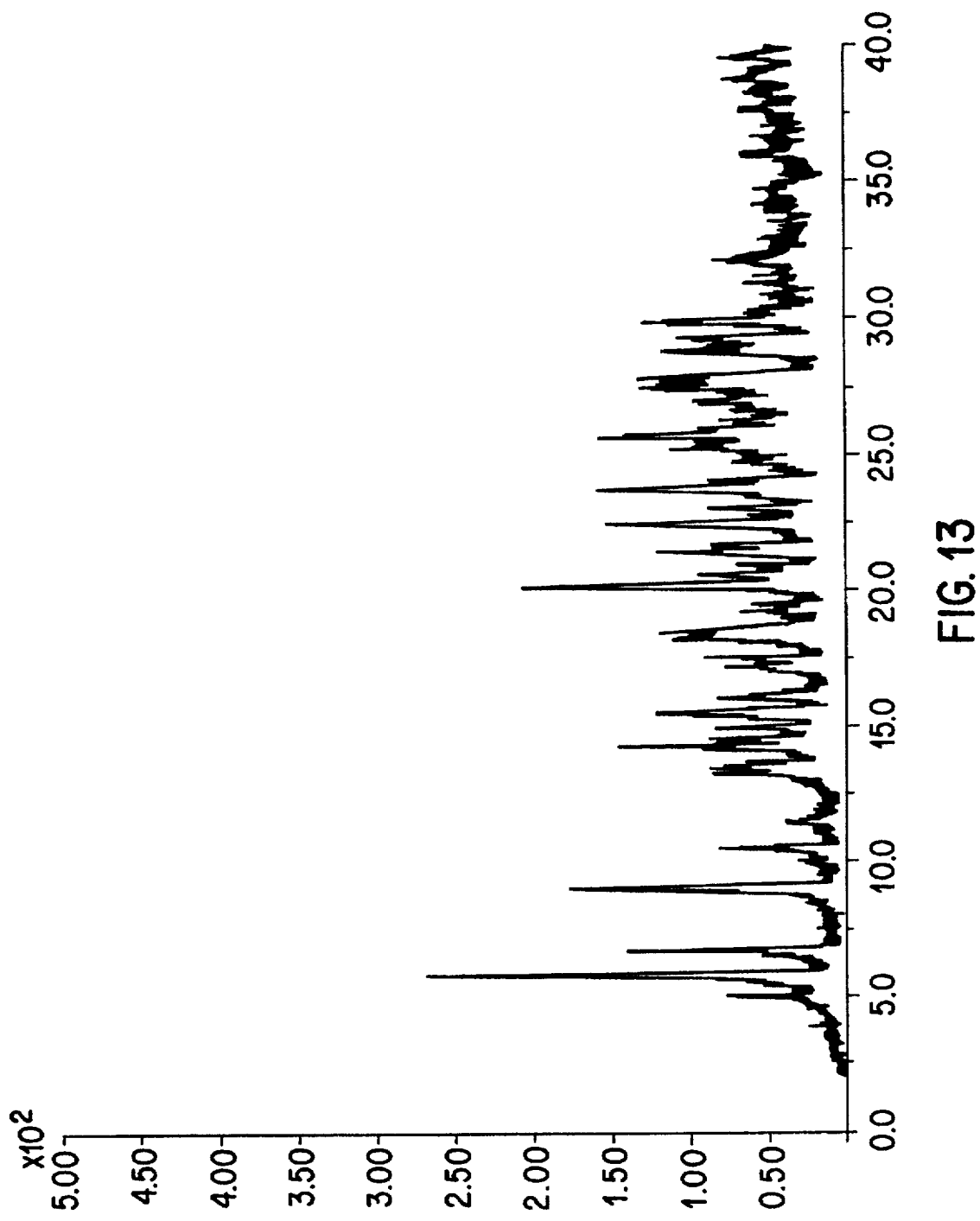
Figure 14:
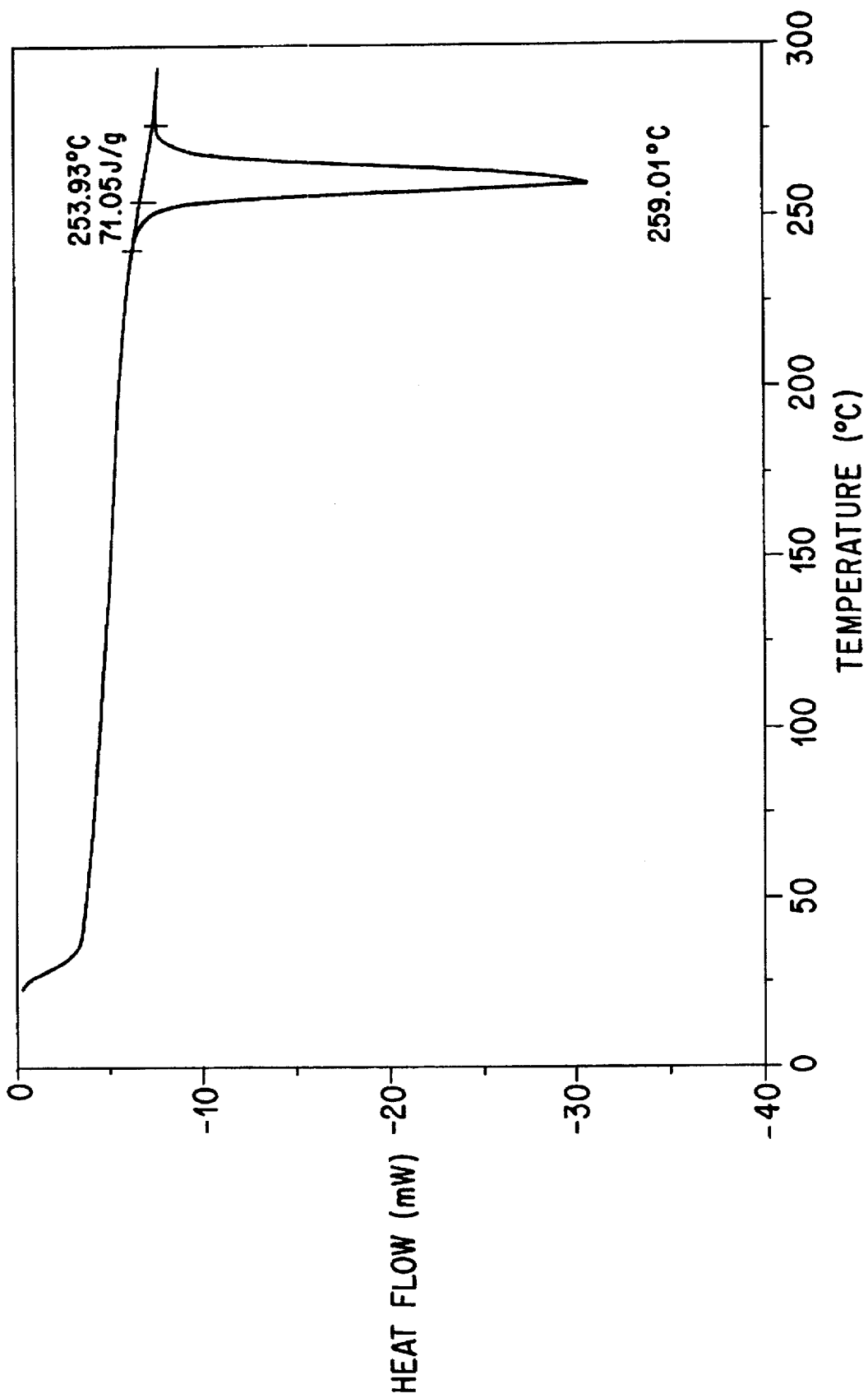

Following the isolation of form "T", the equilibrium water solubility of form "D" was again determined and during this copper K alpha radiation. Below is a list of the key diffraction peaks (2Θ) for the following crystal forms:

| A | B | C | D | E | F | G | I | J | Id | W | H |
|---|---|---|---|---|---|---|---|---|---|---|---|
| 3.82 | 4.97 | 5.34 | 4.19 | 3.84 | 4.5 | 4.84 | 3.81 | 3.67 | 3.62 | 4.35 | 5.78 |
| 7.56 | 5.84 | 7.15 | 8.33 | 7.37 | 9.0 | 5.68 | 7.25 | 7.30 | 7.10 | 7.46 | 6.73 |
| 8.14 | 6.75 | 10.46 | 8.81 | 8.61 | 14 | 6.58 | 8.18 | 8.53 | 8.42 | 8.31 | 9.02 |
| 10.30 | 9.09 | 22.51 | 9.76 | 10.22 | 16 | 8.85 | 8.52 | 10.10 | 9.98 | 9.35 | 10.41 |
| 14.50 | 10.01 | | 12.46 | 11.32 | 21 | 9.77 | 10.33 | 11.42 | 11.18 | 14.91 | 11.55 |
| 15.25 | 10.54 | | 13.63 | 13.50 | | 10.30 | 10.56 | 13.33 | 13.25 | 18.52 | 13.42 |
| | 11.42 | | 14.06 | 14.76 | | 11.35 | 11.3 | 14.77 | 14.56 | 21.04 | 14.33 |
| | 13.26 | | 15.93 | 15.62 | | 13.27 | 12.12 | 15.46 | 16.24 | 25.35 | 15.69 |
| | 13.45 | | 16.88 | 16.87 | | 13.98 | 13.76 | 16.32 | 17.78 | 28.10 | 17.29 |
| | 14.26 | | 17.64 | 17.95 | | 14.23 | 15.38 | 17.95 | 20.43 | 29.68 | 18.36 |
| | 14.50 | | 18.85 | 20.67 | | 14.61 | 15.87 | 20.71 | 22.23 | 32.98 | 20.17 |
| | 14.89 | | 19.34 | 21.63 | | 15.22 | 19.22 | 23.76 | 23.37 | 37.34 | 21.52 |
| | 15.51 | | 22.12 | 22.36 | | 15.99 | 20.61 | 23.92 | 24.79 | | 22.47 |
| | 16.25 | | 24.93 | 23.54 | | 17.09 | 21.55 | 25.30 | 29.30 | | 23.79 |
| | 17.10 | | 26.91 | | | 17.82 | 22.32 | 25.80 | 30.39 | | 25.82 |
| | 17.20 | | | | | 18.11 | 23.46 | | 31.25 | | 27.80 |
| | 17.46 | | | | | 19.83 | 24.89 | | 31.53 | | 28.99 |
| | 18.24 | | | | | 21.25 | 26.26 | | 34.16 | | 30.02 |
| | 19.17 | | | | | 22.67 | | | 36.00 | | |
| | 20.18 | | | | | 23.31 | | | | | |
| | 23.70 | | | | | 25.29 | | | | | | study it converted to form "T". "D" is therefore metastable with respect to "T" and in the energy profile it is at higher energy. After the discovery of form "T", form "D" could no longer be isolated in our laboratory. TGA studies indicate that form "T" of 3-[2'-(N-benzoyl)sulfonamidobiphenyl-4-yl]methyl-5,7-dimethyl-2-ethyl-3H-imidazo[4,5-b]pyridine potassium salt is a dihydrate (FIG. 4). Hygroscopicity studies demonstrated that form "T" is non-hygroscopic at relative humidities of 47% and above. Although form "T" dehydrates at elevated temperatures (60°-170° C.) to form "Id" (FIG. 5) it is reconverted to form "T" upon exposure to ambient humidity.

Based on reproducibility in both the laboratory and production scale crystallizations and thermodynamic stability data from equilibrium solubility studies and solution calorimetric experiments, form "T" of 3-[2'-(N-benzoyl)sulfonamidobiphenyl-4-yl]methyl-5,7-dimethyl-2-ethyl-3H-imidazo[4,5-b]pyridine potassium salt was determined to have the crystal properties needed for pharmaceutical development.

The crystal forms were characterized and evaluated by measuring the heats of solution or solution calorimetry, solubility data, x-ray powder diffraction patterns (XRPD), differential scanning calorimetry (DSC) and thermogravimetric analysis (TGA). Heats of solution at 30° C. were obtained in the Setaram C-80 calvet calorimeter with sample size of 7–13 mg dissolved into 5 ml of 88% DMSO 12% water for a final concentration of 1.4–2.6 mg/ml. XRPD patterns were recorded using an automated Siemens X-ray diffractometer with copper tube K alpha radiation. DSC and TGA were conducted using a Perkin Elmer series 7 instrument with a scan rate of 10° C./min over the temperature range of 30°-300° C. Utilizing these techniques the thermodynamic stability of the polymorphs of 3-[2'-(N-benzoyl)sulfonamidobiphenyl-4-yl]methyl-5,7-dimethyl-2-ethyl-3H-imidazo[4,5-b]pyridine potassium salt was determined.

X-ray powder diffraction (XRPD) patterns were recorded using an automated X-ray diffractometer APD 3720 with The following examples illustrate the preparation of the crystal forms of 3-[2'(N-benzoyl)sulfonamidobiphenyl-4-yl]-methyl-5,7-dimethyl-2-ethyl-3H-imidazo[4,5-b]pyridine potassium salt and as such are not to be considered as limiting the invention set forth in the claims appended hereto.

EXAMPLE 1

3-[2'(N-Benzoyl)sulfonamidobiphenyl-4-yl]-methyl-5,7-dimethyl-2-ethyl-3H-imidazo[4,5-b]pyridine potassium salt Step A: Preparation of 2-amino-5-bromo-4,6-lutidine

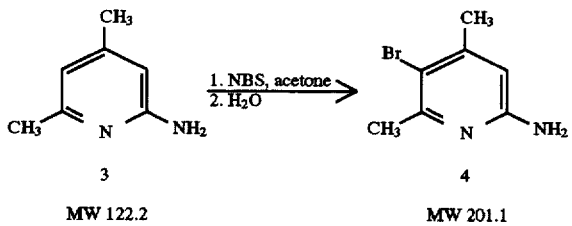

2-Amino-4,6-lutidine (101.0 g, 0.827 mole) is dissolved in acetone at 25° C. and the solution cooled to −15° C. N-Bromosuccinimide (137.5 g, 0.778 mole) is added in 10×13.75 g portions over 1.5 hours, maintaining a temperature of −10° C. After addition is complete, the slurry is aged at −10° C. for 0.5 hours. Water (1820 mL) is added over 0.5 hours, allowing the temperature to rise to 20°-25° C. The resulting slurry is recooled to 5°-10° C. and aged for 1 hour then filtered and the product washed with cold water (500 mL, 5°-10° C.) and dried under vacuum to yield 141.3 g of 2-amino-5-bromolutidine (4) at a purity of 96.9% (HPLC wt %) for a yield of 82.3%. The crystallization as described removes succinimide (water soluble), 2-amino-4,6-lutidine (3) (water soluble) and 2-amino-3-bromo-4,6-lutidine (10). The 2-amino-3,5-dibromo-4,6-lutidine (8) co-crystallizes with the product and remains as a 2–3% impurity. HPLC conditions: Zorbax C-8, flow-1.5 mL/minutes, UV detection at 280 nm, eluant—$CH_3CN$:0.01M $H_3PO_4$, 30:70 isocratic. Retention times: 2-amino-5-bromo-4,6-lutidine (4)—4.4 minutes; and 2-amino-3,5-dibromo-4,6-lutidine (8)—6.1 minutes.

Step B: Preparation of 2-amino-5-bromo-3-nitro-4,6-lutidine (5)

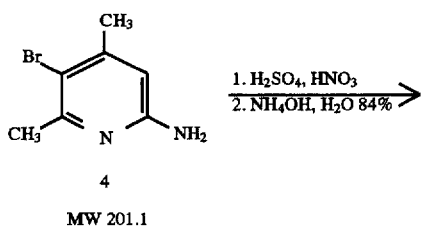

4
MW 201.1

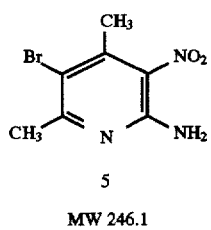

5
MW 246.1

Sulfuric acid (600 mL, 96–98%) is charged to a 1-L round bottomed flask and cooled to 10° C. and 2-amino-5-bromo-4,6-lutidine (4, 119.5 g @97% purity, 0.576 mole) is added in portions over 1 hour. The solution is cooled to 10° C. and 70% nitric acid (37.0 mL, 0.575 mole) is added over 1 hour, maintaining a temperature <25° C. The progress of the reaction is monitored for completion by HPLC. The yellow solution is aged at 25° C. for 1 hour. HPLC conditions: Zorbax RX-C8, flow—1.5 mL/minutes, UV detection at 280 nm, gradient elution as follows: at 0 min., 30:70 $CH_3CN:0.01M$ $H_3PO_4$; 5 min., 30:70 $CH_3CN:0.01M$ $H_3PO_4$; at 10 min., 60:40 $CH_3CN:0.01M$ $H_3PO_4$; at 15 min., 60:40 $CH_3CN:0.01M$ $H_3PO_4$. Retention times: 2-amino-5-bromo-4,6-lutidine (4), 1.8 minutes; 2-amino-5-bromo-3-nitro-4,6-lutidine (5), 12.7 minutes; 2-amino-5-bromo-4,6-diemthyl-2-pyridone (9), 5.6 minutes; and 2-nitramino-5-bromo-4,6-lutidine (11), 11.1 minutes. The reaction mixture is added to chilled water (5°–10° C.) (3.0 L), maintaining the quench temperature <25° C. The mixture is neutralized with concentrated aqueous ammonium hydroxide (1.45 L) to a pH of 7–8. The resultant slurry is filtered and the yellow product washed with water and dried under vacuum to yield 137.2 g of 2-amino-5-bromo-3-nitro-4,6-lutidine (5) at a purity of 87.6% (HPLC wt % for a yield of 84%.

Step C: Preparation of 5,7-dimethyl-2-ethylimidazo[4,5-b]pyridine (7)

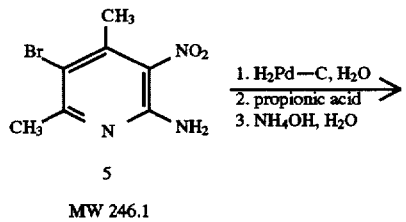

5
MW 246.1

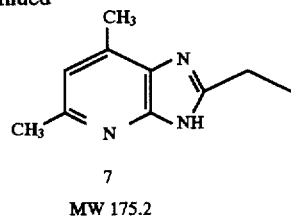

7
MW 175.2

2-Amino-5-bromo-3-nitro-4,6-lutidine (5, 57.2 g at 87% purity, 0.204 mole) is charged to a vessel containing 4% aqueous sodium hydroxide (500 ml, 0.5 mole) and THF (100 mL). 5% Palladium on carbon (1.0 g) is added and the slurry is hydrogenated in a glass bottle on a Parr shaker at 40 psi hydrogen at 25° C. until the theoretical amount of hydrogen is consumed. Addition of the bromo-nitro-lutidine (5) should be made after the THF and aqueous NaOH have been premixed. This prevents the formation of lumps and aids in the wetting of the solid. 3 Moles of hydrogen are required. Use of excess catalyst (>2 wt %) results in a rapid hydrogen uptake and an exotherm difficult to control by external cooling. The end point is marked by complete cessation of hydrogen uptake. Analysis by gas chromatography confirms complete reaction. Typically, <1% of the bromo-diamino intermediate remains. G.C. conditions: DB-5 (25 m×0.22 mm), flow—1.0 mL/minutes helium, constant flow mode, inj. temp—250°, det. temp. 300° C., ramp from 110° C. (2 minutes) to 280° C. at 10° C./minutes. Retention times: 2,3-diamino-4,6-lutidine, 8.8 minutes; 5-bromo-2,3-diamino-4,6-lutidine, 12.7 minutes; and 2-amino-5-bromo-3-nitro-4,6-lutidine (5), 12.4 minutes. Propionic acid (500 mL) is added to the mixture and the catalyst is removed by filtration through a pad of solka-foc (1 g). The filter cake is washed with propionic acid (100 mL). The combined filtrates are concentrated by distillation at atmospheric pressure to one-half volume. Propionic acid (200 mL) is added and distillation continued until the batch temperature reaches 147°–149° C. The mixture is heated under reflux for 5 hours at a reaction temperature of 147°–149° C. Periodic distillation to remove water (a reaction by-product) is required to maintain this reaction temperature. A batch temperature of >145° C. is required for complete cyclization. The reaction is considered complete when <3% of the 2,3-diaminolutidine+monoacyl-2,3-diaminolutidine remains by G.C., retention times—12.4 minutes and 13.4 minutes respectively. The final reaction volume is adjusted to 350 mL by addition of propionic acid or further concentration. The homogeneous solution is cooled to 40° C. and water (250 mL) is added. The pH is adjusted to 9.0–9.5 by the addition of concentrated ammonium hydroxide (270 mL) maintaining the temperature at 30°–50° C. The solution is cooled to 15° C. and the slurry is aged for 1 hour. The slurry is aged at −5° C. for 1 hour. The slurry is filtered and washed well with cold water (2° C., 300 mL) and dried under vacuum with a nitrogen purge at 30° C. to yield 27.6 g of the imidazolutidine (7) at a purity of 100% (HPLC wt %) for a yield of 78%.

Step D: Preparation of 5,7-Dimethyl-2-ethyl-3-(4-bromobenzyl)imidazo[4,5-b]pyridine (2)

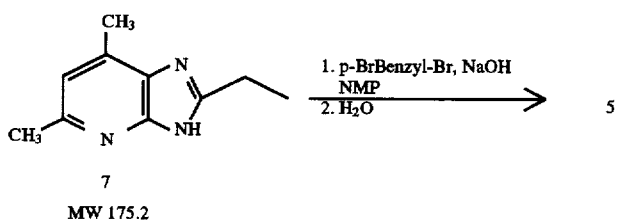

7
MW 175.2

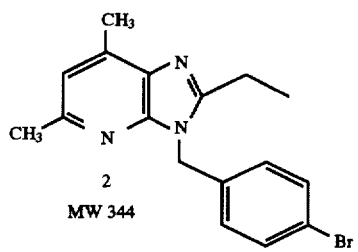

2
MW 344

2-Ethylimidazo-4,6-lutidine (52.9 g, 0.302 mol) is dissolved in N-methylpyrrolidinone (NMP) (212 mL) at 20° C. An aqueous solution of sodium hydroxide (50%, 36.2 g, 0.453 mol) is added over 5 minutes. The mixture is maintained at 20°–25° C. for 30 minutes, cooled to 0° C. and 4-bromobenzyl bromide (77.1 g, 0.308 mol) in NMP (55 ml) is added over 0.5 hours maintaining the temperature at 0°–5° C. and aged at that temperature for 3 hours. Water (314 mL) is slowly added over 0.5 hours maintaining a temperature of 5°–10° C. Additional water (630 mL) is added over 0.5 hours, allowing the temperature to rise to 20° C. and aged at that temperature for 1 hour. The slurry is filtered and the product washed with NMP:water (1:3 v:v, 200 mL) then water (500 mL) and dried under vacuum at 30°–40° C. to yield 91.8 g of the benzylated imidazolutidine (2) at a purity of 97.8% (HPLC wt %) for a yield of 77%.

Step E: Purification of 5,7-Dimethyl-2-ethyl-3-(4-bromobenzyl)imidazo[4,5-b]-pyridine 5,7-Dimethyl-2-ethyl-3-(4-bromobenzyl)imidazo[4,5-b]-pyridine, 2 (40 g, 0.113 mol.) and Darco G60 (4 g) are suspended in acetone (240 mL) and the mixture is heated at 40° C. for 1 hour. The mixture is hot-filtered at 40° C. through a pad of Celite (5.0 g) and the charcoal/Celite cake is washed with warm acetone (50 mL). The filtrate volume is reduced in vacuo to 240 mL. While maintaining the acetone solution at 40° C., water (144 mL) is added. The mixture is cooled to 37° C. and, with good agitation, aged until crystallization occurred. If necessary, seeding can be done at this point. After the mixture is cooled to 0°–5° C. over 1 hour and aged at that temperature for 1 hour, water (336 mL) is then added over 1 hour while maintaining the internal temperature at <10° C. The slurry is further aged at 0°–5° C. for 1 hour, filtered, and the cake is washed with cold water (100 mL). The wet product is dried in vacuo at 50° C. with a slight nitrogen bleed. The recovery is 38.6 g (96.5% corrected for 97 wt % purity).

Step F: Preparation of t-Butylbenzenesulfonamide 15

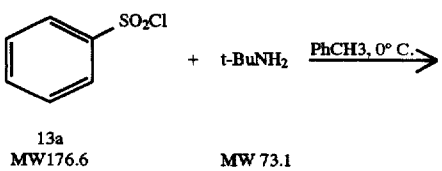

13a
MW176.6        MW 73.1

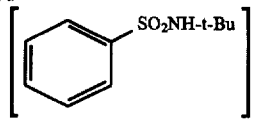

13b
MW213.2

A 1-L round-bottomed flask under nitrogen is equipped with a dropping funnel. Toluene (110 mL; KF<100 mcg/mL) and t-butylamine (69 mL, 0.66 mol, d=0.696; KF<100 mcg/mL) are charged into the flask. A mixture of benzensulfonyl chloride (38 mL, 0.30 mol, d=1.384) and toluene (200 mL) is charged into the addition funnel and this solution is added to the amine dropwise over 0.75 h, maintaining a temperature between 25°–33° C. When the addition is complete, the solution is aged for 1 hour at 30° C. The progress of the reaction is monitored by HPLC. HPLC conditions: column: Zorbax RX-C8; gradient elution of $CH_3CN$/water/$H_3PO_4$ from 30:70:0.1 to 60:40:0.1 in 15 min.; flow rate—1.0 mL/min.; UV detection at 228 nm.; and retention time: sulfonamide 13b, 14.1 min. A 3N aqueous hydrochloric acid solution is added dropwise, maintaining the temperature <40° C. The layers are separated and the organic phase is washed with water (290 mL). The organic phase is concentrated to a volume of 150 mL by distillation at atmospheric pressure which contains 58.2 assay grams of tert-butylbenzenesulfonamide (13b) for a 93 % yield. The KF of the final solution is 70 mcg/mL.

Step G: Preparation of t-Butyl sulfonamidophenylboronic acid

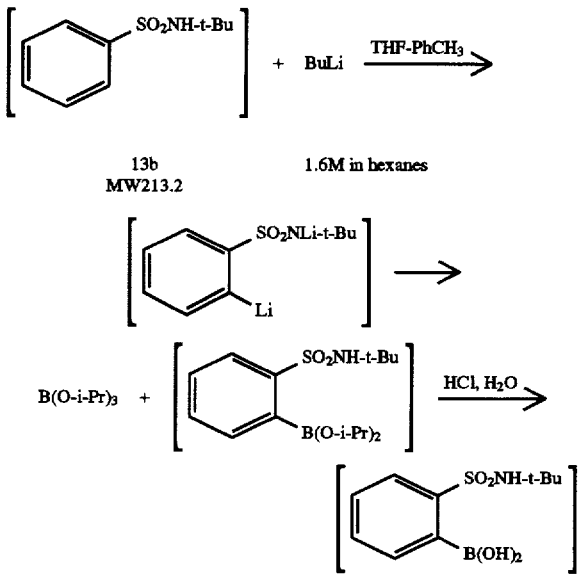

13
MW 257

A 3-liter 3-necked flask is equipped with an overhead stirrer, a nitrogen inlet and an addition funnel. The flask is charged with tetrahydrofuran (256 mL; KF<70 mcg/mL) and the toluene solution of the sulfonamide 13b (125 mL containing 48.5 g, 0.228 mol, 1.8M solution in toluene- 0.389 g/mL). The mixture is cooled to 1° C. The KF of the solution is 70 mcg/mL. The n-butyllithium (1.6M in hexanes, 302 mL, 0.48 mol) is charged into the addition funnel and added dropwise over 55 min., maintaining a temperature <5° C. The mixture is aged for 2 hours and triisopropylborate (63 mL, 0.273 mol, d=0.815) is added to the suspension over 70 min. The temperature is maintained <2° C. After 1 hour, the reaction is 94% complete by HPLC. The reaction must be quenched once the assay indicates completion since the product will slowly decompose in the reaction mixture. HPLC conditions: column: Zorbax RX-C8; gradient elution with $CH_3CN$/water/$H_3PO_4$ from 30:70:0.1 to 60:40:0.1 over 15 min.; flow rate=1.0 mL/min.; UV detection at 228 nm.; Retention time: t-Butyl sulfonamidophenylboronic acid 13, 8.5 min. The reaction is quenched by the addition of water (50 mL) at 0° C. The temperature is maintained <10° C. Concentrated hydrochloric acid (42 mL) is added dropwise, maintaining the temperature <10° C. The layers are separated and the organic phase is washed with water (50 mL), then brine (50 mL). The organic phase is concentrated to 100 mL under vacuum at an internal temperature <30° C. The solution is diluted to 350 mL with n-butanol and concentrated to 225 mL under vacuum providing a 1M solution of the sulfonamido phenylboronic acid 13 (54 g) for a 90% yield. The vacuum concentration at an internal temperature <30° C. is required to minimize deboronation. A concentration range of 0.8–1.2M in butanol has performed successfully in the subsequent coupling reaction.

Step H: Preparation of 3-[2'-(N-t-Butyl) sulfonamidobiphenyl-4-yl]-methyl-5,7-dimethyl-2-ethyl-3H-imidazo[4,5-b]pyridine

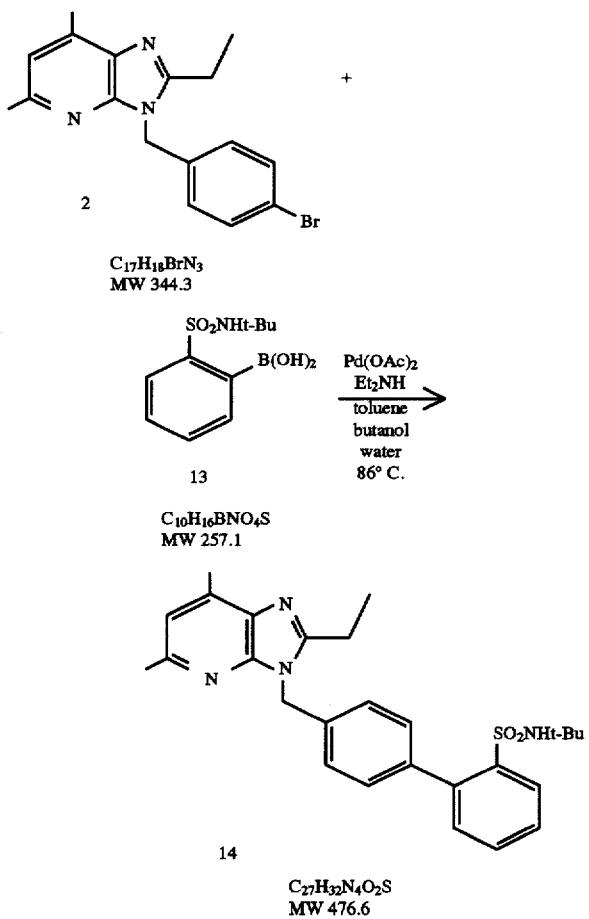

Catalyst Preparation

Triphenylphosphine (0.304 g, $1.16\times10^{-3}$ mol, d=0.707) is dissolved in toluene (25 mL) and the solution is degassed with vacuum/nitrogen purges (3×). Palladium acetate (0.065 g, $2.91\times10^{-4}$ mol) is added and the solution is degassed again (3×). The resulting solution is warmed to 60° C. under nitrogen for 30 min. and then cooled to 25° C.

Coupling Reaction

A round-bottomed flask is equipped with a magnetic stirrer, $N_2$ inlet and a condenser. The flask is charged with toluene (57 mL), 5,7-dimethyl-2-ethyl-3-(4-bromobenzyl) imidazo[4,5-b]-pyridine, 2 (5.1 g at 98% by weight), 0.0145 mol), t-butylsulfonamidophenylboronic acid, 13 (23.2 mL of butanol solution at 0.193 g/mL, 4.48 g, 0.0174 mol) and deionized $H_2O$ (19 mL). The mixture is degassed with vacuum/nitrogen purges (3×), and then degassed diethylamine (3.6 mL, 0.035 mol) is added. Then the catalyst solution is added and the mixture is heated to reflux for 4 hours, whereupon HPLC shows no 5,7-dimethyl-2-ethyl-3-(4-bromobenzyl)imidazo[4,5-b]-pyridine, 2 remaining. HPLC conditions: Zorbax RX-C8, acetonitrile:water: phosphoric acid, gradient elution from 35:65:0.1 to 90:10:0.1 in 12 minutes, hold 8 minutes, flow=1.0 mL/minutes and UV detection at 228 nm. Retention times: t-butylsulfonamidophenyl-boronic acid, 13, 6.8 minutes; 5,7-dimethyl-2-ethyl-3-(4-bromobenzyl)imidazo[4,5-b]-pyridine, 2, 7.5 minutes; and 3-[2'-(N-t-Butyl) sulfonamidobiphenyl-4-yl]-methyl-5,7-dimethyl-2-ethyl-3H-imidazo[4,5-b]pyridine, 14, 9.2 minutes.

The reaction mixture is cooled to 50° C. and the aqueous phase is separated from the organic phase. Tributylphosphine (0.36 mL, $1.45\times10^{-3}$ mol, d=0.812) is added with stirring. The solution is concentrated to 50 mL at reduced pressure (200 mm Hg, 70° C.). Hexanes (100 mL) are added dropwise over 30 minutes with stirring at 50° C., then the suspension is cooled to room temperature over one hour, then aged at 0° C. for one hour. The off-white solid is filtered and washed with 15 mL of cold 2:1 hexanes:toluene and dried overnight in vacuo with a nitrogen purge at 40° C. to afford 6.36 g of an off-white solid. The yield of this reaction is 91% (corrected for 99 wt % purity). There is 20 ppm residual Pd in the batch.

Step I: 3-[2'-sulfonamidobiphenyl-4-yl]methyl-5,7-dimethyl-2-ethyl-3H-imidazo[4,5-b]pyridine

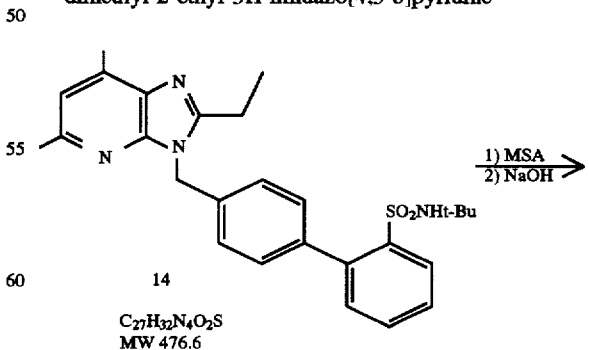

15
-continued

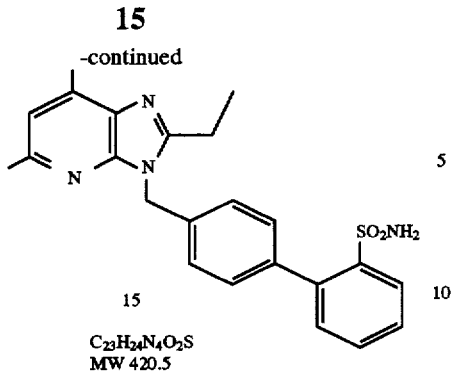

15

C₂₃H₂₄N₄O₂S
MW 420.5

Biphenyl-t-butylsulfonamide 14 (20.0 g, 0.041 mol) is added to a two-phase mixture of methanesulfonic acid (MSA) (35.0 mL, 0.54 mol) and toluene (40.0 mL) in 4 portions over a period of 30 minutes, while maintaining the solution temperature at 30° to 40° C. Moisture should be excluded from the reaction mixture. In between the additions, the mixture must be kept under nitrogen. The two-phase mixture is aged at 35° to 40° C. until the deprotection is >99 A % complete (2 to 3 hours). The mixture is diluted carefully with water (70.0 mL). The lower aqueous layer is separated and the toluene layer is extracted with water (5 mL). The combined aqueous layer is then filtered. The filtrate is added slowly to the mixture of 50 wt % aqueous sodium hydroxide (42.9 g) and tetrahydrofuran (THF) (300.0 mL) at ≦40° C. The pH of the solution is finally adjusted to 6.0 to 8.0 with either MSA or sodium hydroxide depending on the pH of the solution after charging the aqueous MSA filtrate. The aqueous layer is removed. The volume of the mixture is reduced by atmospheric distillation to 33% (~100 mL). The volume is then doubled (to ~200 mL) by the slow addition of isopropyl acetate white maintaining the temperature at 60° to 65° C. The remaining THF is removed completely by atmospheric distillation and replaced with i-propyl acetate. The slurry is cooled to 20° C. and aged for 1 hour. The crystallized product is filtered and washed with cold isopropyl acetate (30 mL). The isolated product is dried at ≦40° C. The yield is 16.3 g (92% yield corrected for 97 wt % purity).

Step J: Preparation of 3-[2'-(N-benzyl) sulfonamidobiphenyl-4-yl]methyl-5,7-dimethyl-2-ethyl-3H-imidazo[4,5-b]pyridine

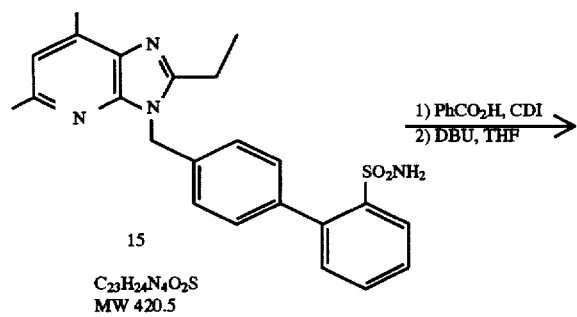

15

C₂₃H₂₄N₄O₂S
MW 420.5

16
-continued

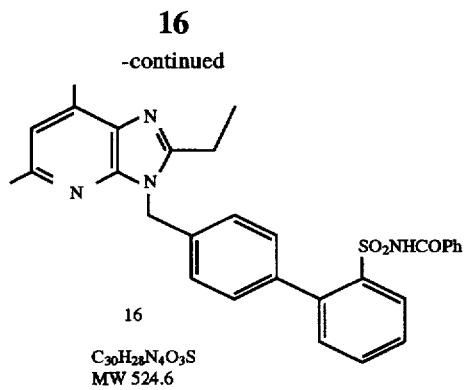

16

C₃₀H₂₈N₄O₃S
MW 524.6

Sieve-dried THF (35 mL, KF<20 μg/mL H₂O), carbonyldiimidazole (2.74 g, 0.0166 mol) and benzoic acid (2.03 g, 0.0166 mol) are charged into a flask equipped with a magnetic stirrer, N₂ inlet and condenser. The solution is heated over 1 hour to 60° C. The CO₂ evolution is continuous and moderate. After an additional hour, the CO₂ evolution has ceased and the solution is cooled to 22° C. with an ice-water bath. The sulfonamide 15 (5.15 g at 97 wt % purity, 0.0119 mol) is charged followed by 1,8-diazabicyclo[5.4.0]undec-7-ene (DBU) (2.48 mL, 0.0166 mol). The solution is aged at 60° C. for 1 hour. To the hot solution is added 23 mL of deionized H₂O, followed by 23 mL of i-propyl acetate. Phosporic acid is added dropwise until the pH of the solution is 3.5. The aqueous phase is separated and the organic phase is washed with 10 mL of 1:1 saturated brine: H₂O. The organic phase is concentrated in vacuo (135 mm Hg) at 30° C. to 35 mL, then diluted with 45 mL of isopropyl acetate and concentrated again to 35 mL. The suspension is cooled over 30 minutes to 20° C., then to 0° C. and aged at that temperature for one hour. The product is collected by suction filtration and washed with 10 mL of cold (0° C.) i-propyl acetate. After air drying in vacuo (150 mm Hg) with a N₂ purge for 2 hours at 40° C., the yield of the crude product is 5.92 g (93% yield, corrected for 98.5 wt % purity).

Isopropyl Acetate Swish (if necessary)

The crude product from above (4.0 g) is suspended in i-propyl acetate (20 mL) and heated to reflux. The suspension is aged at reflux for 2 hours, cooled to 20° C. over 30 minutes, then to 0° C. and aged at that temperature for one hour. The product is collected by filtration and washed with 8 mL of cold (0° C.) i-propyl acetate. The solid is dried in vacuo with a N₂ purge for 18 hours at 40° C., to afford 3.92 g of product 16 (97% recovery and 99 wt % pure). The overall yield of the reaction and the swish is 90%.

Step K: Preparation of 3-[2'-(N-Benzyl) sulfonamidobiphenyl-4-yl]methyl-5,7-dimethyl-2-ethyl-3H-imidazo[4,5-b]pyridine potassium salt—(Forms I, I_d and W)

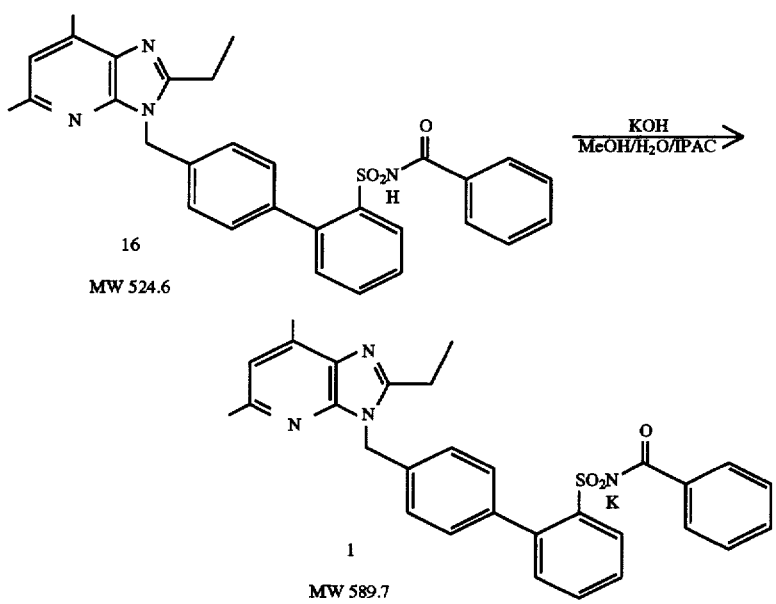

16
MW 524.6

1
MW 589.7

In a 72-L four-necked flask fitted with an overhead stirrer and a reflux condenser, 3-[2'-(N-benzyl) sulfonamidobiphenyl-4-yl]methyl-5,7-dimethyl-2-ethyl-3H-imidazo[4,5-b]pyridine 1 (5.04 kg, 9.6 mol), methanol (14.5 L) and water (2.5 L) are mixed. The slurry is warmed to 62° C. under a nitrogen atmosphere and 1.94M potassium hydroxide (4.96 L, 9.61 mol) is added to the slurry at 62° C. over 1.5 hours to provide a homogeneous solution. Isopropyl acetate (13.83 L) is then added at 65° C. and the mixture is warmed to 70° C. The homogeneous solution is filtered at 70° C. to remove any particulates that are present. The filtrate is diluted with isopropyl acetate (1.3 L), methanol (0.6 L) and water (0.1 L). The solubility of the potassium salt at 60° C. in 1:2:2 water/methanol/isopropyl acetate is 174 mg/mL. The homogeneous mixture is cooled to 52° C. over 2 hours, whereupon potassium salt seed of form "T" (140 g) is added. This mixture becomes cloudy after 30 min. The mixture is aged for 10 hours at 52° C. The white slurry is cooled to 48° C. over 1 hour and stirred for 3 hours. Finally, the crystallization mixture is cooled to 0° C. at a rate of 1° C./12.5 min. and aged for 2 hours at 0° C. The solubility of 3-[2'-(N-benzyl)sulfonamidobiphenyl-4-yl]methyl-5,7-dimethyl-2-ethyl-3H-imidazo[4,5-b]pyridine potassium salt at 0° C. in 1:2:2 water/methanol/isopropyl acetate is 15 mg/mL. The solid is centrifuged at 0° C. and displacement-washed with a mixture of 2:2:1 cold (0° C.) isopropyl acetate/methanol/water (5.65 L) followed by isopropyl acetate (2.3 L). The solid is semi-dried to a TG of 10–15% by spin drying. The mother liquors contain 21 wt % of 3-[2'-(N-benzyl)sulfonamidobiphenyl-4-yl]methyl-5,7-dimethyl-2-ethyl-3H-imidazo[4,5-b]pyridine potassium salt. At this stage, the crystal form of the product is form "W". The product is powdered by passing through a screen (size=12). The solid is dried by passing dry nitrogen over the solid under vacuum at 22° C. for 5 hours to yield 4.55 kg of 3-[2'-(N-benzyl)sulfonamidobiphenyl-4-yl]methyl-5,7-dimethyl-2-ethyl-3H-imidazo[4,5-b]pyridine potassium salt as the form "T" with a purity of 99.7% (assay-HClO₄ titration) and TG of 7–10%. Generally, the wet cake consists of residual water, methanol and isopropyl acetate. The K-salt is considered dry when <0.05% methanol and isopropyl acetate are detected by $^1$H NMR. The product is further powdered by passing the solid through a Quadro Comil (model 197s, screen size=1143 mm round impeller) to yield 4.5 kg. The product is dried to a TG of 4.6–5.5% by the passage of dry nitrogen over the solid under vacuum at 22° C. After 10 hours, 4.24 kg (78%) of the potassium salt as the form "T" is obtained with a TG of 6.1% (99.7 wt % by titration). The water content can be monitored by TG analysis. The TG of the potassium salt of form "T" is 4.6–5.5%. The crystal form is monitored by X-ray analysis. When the potassium salt is over dried, the crystal form converts to form "Id" (TG<4.6%). If this occurs, the salt can be re-equilibrated to form "T" by passing wet nitrogen (relative humidity (RH)=~50%) over the potassium salt.

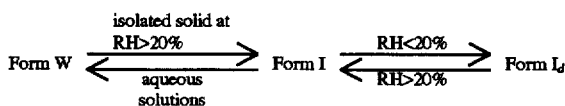

HPLC Conditions: column: Phenyl-5 mm Zorbax Stabilbond, 25 cm×0.46 cm; column temperature: 25° C.; gradient of 90:10 to 10:90 over 30 minutes 0.1% $H_3PO_4$: acetonitrile and 10:90 0.1% $H_3PO_4$: acetonitrile for 5 minutes; flow rate 1.5 mL/minutes; wavelength: 220 nm; and sample preparation: 0.3 mg/mL.; and retention times: sulfonamide, 12.2 minutes; arylbromide, 14.4 minutes; 3-[2'-(N-benzoyl)sulfonamidobiphenyl-4-yl]methyl-5,7-dimethyl-2-ethyl-3H-imidazo[4,5-b]pyridine potassium salt, 1, 16.5 minutes; and t-butylsulfonamide, 17.1 minutes.

EXAMPLE 2

3-[2'-(N-Benzoyl) sulfonamide-biphenyl-4-yl]methyl-5,7-dimethyl-2-ethyl-3H-imidazo[4,5-b]pyridine potassium salt (Form B)

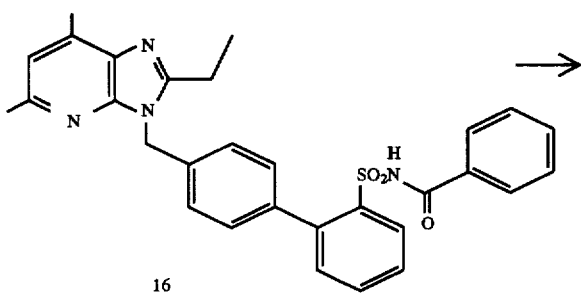

16

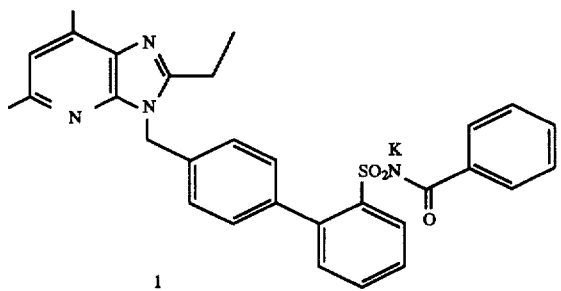

1

The free acid 16 (1.022 g, 1.95 mol) was slurried in methanol (20 L), and the mixture was warmed to 25°–30° C. The solution was then charged with freshly titrated 0.92M potassium hydroxide-methanol solution (2.125 L, 1.955 mol). The addition of the KOH was done incrementally and the pH was monitored. To the orange-yellow batch was added Darco G-60 (50 gm). Heat to 40°–45° C., age for 15 minutes, then filter through solka-floc (100 gm—prewashed with hot methanol 5L). The batch was concentrated to ~12 L at 1 atmosphere, diluted with filtered isopropylacetate (IPAC) 17 L, and reconcentrated to ~12 L. The batch was diluted with filtered IPAC (17 L), and concentrated to 18 L. When the batch volume was ~25 L (temp.=72°–73° C.), the mixture turned to a thick paste. The batch was diluted with filtered IPAC (10 L) and concentrated to ~20 L, which requires 9 hours. The internal temperature rises slowly to 85°–86° C. over the nine-hour reflux period. The final temperature was 86° C. The batch starts to thin and thicken after about 5–6 hours from the time it becomes thick. The batch never completely mined into a thin slurry. The batch was cooled to 20° C. and filtered. Filtration requires ~30 minutes. The flask and cake were washed with IPAC (3×1 L). The cake was air dried with suction, under $N_2$ for 30 h to afford 1146 gm of a fluffy whim solid. The batch was placed on trays and dried in a vacuum oven at 125° C. with a $N_2$ purge for 12 h to afford 1075 gm (98%) of a free-flowing white solid. A crystal form B sample of the solid was assayed by $^1H$ NMR and showed <0.5% (mol %) of IPAC. There was also ~1.5–2.0 mol % of KOAc (singlet at δ=1.9 ppm).

EXAMPLE 3

3-[2'-(N-Benzoyl)sulfonamide-biphenyl-4-yl]methyl-5,7-dimethyl-2-ethyl-3H-imidazo[4,5-b]pyridine potassium salt (Form D)

A suspension of 3-[2'-(N-benzoyl)sulfonamidobiphenyl-4-yl]methyl-5,7-dimethyl-2-ethyl-3H-imidazo[4,5-b]pyridine potassium salt in water is shaken at room temperature overnight. The suspension is filtered and the remaining solid dried at room temperature.

EXAMPLE 4

3-[2'-(N-Benzoyl)sulfonamide-biphenyl-4-yl]methyl-5,7-dimethyl-2-ethyl-3H-imidazo[4,5-b]pyridine potassium salt (Form F)

3-[2'-(N-Benzoyl)sulfonamidobiphenyl-4-yl]methyl-5,7-dimethyl-2-ethyl-3H-imidazo[4,5-b]pyridine potassium salt (Form D) was heated to 40° C. for 24 hours.

EXAMPLE 5

3-[2'-(N-Benzoyl)sulfonamide-biphenyl-4-yl]methyl-5,7-dimethyl-2-ethyl-3H-imidazo[4,5-b]pyridine potassium salt (Form G)

3-[2'-(N-Benzoyl)sulfonamidobiphenyl-4-yl]methyl-5,7-dimethyl-2-ethyl-3H-imidazo[4,5-b]pyridine potassium salt (Form D or F) was heated to between 190°–200° C. for a few minutes.

EXAMPLE 6

3-[2'-(N-Benzoyl)sulfonamide-biphenyl-4-yl]methyl-5,7-dimethyl-2-ethyl-3H-imidazo[4,5-b]pyridine potassium salt (Form I)

A suspension of 3-[2'-(N-benzoyl)sulfonamidobiphenyl-4-yl]methyl-5,7-dimethyl-2-ethyl-3H-imidazo[4,5-b]pyridine potassium salt (Forms A and D) in acetonitrile was stirred at room temperature overnight. The suspension is filtered and the remaining solids were vacuum dried overnight at room temperature.

EXAMPLE 7

3-[2'-(N-Benzoyl)sulfonamide-biphenyl-4-yl]methyl-5,7-dimethyl-2-ethyl-3H-imidazo[4,5-b]pyridine potassium salt (Form J)

A suspension of 3-[2'-(N-benzoyl)sulfonamidobiphenyl-4-yl]methyl-5,7-dimethyl-2-ethyl-3H-imidazo[4,5-b]pyridine potassium salt (Forms B and C) in acetonitrile was stirred at room temperature overnight. The suspension is filtered and the remaining solids were vacuum dried overnight at room temperature.

EXAMPLE 8

3-[2'-(N-Benzoyl)sulfonamide-biphenyl-4-yl]methyl-5,7-dimethyl-2-ethyl-3H-imidazo[4,5-b]pyridine potassium salt (Form H)

3-[2'-(N-Benzoyl)sulfonamidobiphenyl-4-yl]methyl-5,7-dimethyl-2-ethyl-3H-imidazo[4,5-b]pyridine potassium salt (Form I) was heated to about 216° C. for about 3–4 hours.

What is claimed is:

1. Form A of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 3.82, 7.56, 8.14, 10.30, 14.50, and 15.25.

2. Form A of 3-[2'-(N-benzoyl)sulfonamidobiphenyl-4-yl]methyl-5,7-dimethyl-2-ethyl-3H-imidazo[4,5-b]pyridine potassium salt as recited in claim 1 which is additionally characterized by about a 3.4% weight loss upon heating from 30° C. to about 150° C. using thermogravimetric analysis; and a heat of solution in dimethylsulfoxide at 30° C. of about 4.92 J/g.

3. Form B of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 4.97, 5.84, 6.75, 9.09, 10.01, 10.54, 11.42, 13.26, 13.45, 14.26, 14.50, 14.89, 15.51, 16.25, 17.10, 17.20, 17.46, 18.24, 19.17, 20.18, and 23.70.

4. Form B of 3-[2'-(N-benzoyl)sulfonamidobiphenyl-4-yl]methyl-5,7-dimethyl-2-ethyl-3H-imidazo[4,5-b]pyridine potassium salt as recited in claim 3 which is additionally characterized by about a 0.5% weight loss upon heating from 30° C. to about 150° C. using thermogravimetric analysis; and a heat of solution in dimethylsulfoxide at 30° C. of about 17.78 J/g.

5. Form C of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 5.34, 7.15, 10.46, and 22.51.

6. Form C of 3-[2'-(N-benzoyl)sulfonamidobiphenyl-4-yl]methyl-5,7-dimethyl-2-ethyl-3H-imidazo[4,5-b]pyridine potassium salt as recited in claim 5 which is additionally characterized by about a 0.6% weight loss upon heating from 30° C. to about 150° C. using thermogravimetric analysis; a heat of solution in dimethylsulfoxide at 30° C. of about 29.75 J/g.

7. Form D of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 4.19, 8.33, 8.81, 9.76, 12.46, 13.63, 14.06, 15.93, 16.88, 17.64, 18.85, 19.34, 22.12, 24.93, and 26.92.

8. Form D of 3-[2'-(N-benzoyl)sulfonamidobiphenyl-4-yl]methyl-5,7-dimethyl-2-ethyl-3H-imidazo[4,5-b]pyridine potassium salt as recited in claim 7 which is additionally characterized by a solubility in water of 10.4 mg/mL; about a 12 to about a 14% weight loss upon heating from 30° to about 150° C. using thermogravimetric analysis; a heat of solution in dimethylsulfoxide at 30° C. of about −1.36 J/g.

9. Form E of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 3.84, 7.37, 8.61, 10.22, 11.32, 13.50, 14.76, 15.62, 16.87, 17.95, 20.67, 21.63, 22.36, and 23.54.

10. Form F of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 4.5, 9.0, 14, 16 and 21.

11. Form G of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 4.84, 5.68, 6.58, 8.85, 9.77, 10.30, 11.35, 13.27, 13.98, 14.23, 14.61, 15.22, 15.99, 17.09, 17.82, 18.11, 19.83, 21.25, 22.67, 23.31, and 25.29.

12. Form G of 3-[2'-(N-benzoyl)sulfonamidobiphenyl-4-yl]methyl-5,7-dimethyl-2-ethyl-3H-imidazo[4,5-b]pyridine potassium salt as recited in claim 11 which is additionally characterized by a lack of weight loss upon heating from 30° C. to about 150° C. using thermogravimetric analysis and a heat of solution in dimethylsulfoxide at 30° C. of about 8.51 J/g.

13. Form I of 3-[2'-(N-benzoyl)sulfonamidobiphenyl-4-yl]methyl-5,7-dimethyl-2-ethyl-3H-imidazo[4,5-b]pyridine potassium salt characterized by an endothermal maximum of conversion at an onset temperature of about 216° C. when heated in an open pan in a differential scanning calorimetric thermogram at a rate of 20° C./min under a nitrogen atmosphere and which is additionally characterized by about a 4.1% to about a 5.9% weight loss upon heating from 30° C. to about 150° C. using thermogravimetric analysis.

14. Form I of 3-[2'-(N-benzoyl)sulfonamidobiphenyl-4-yl]methyl-5,7-dimethyl-2-ethyl-3H-imidazo[4,5-b]pyridine potassium salt as recited in claim 13 which is additionally characterized by having X-ray powder diffraction angles: 3.81, 7.25, 8.18, 8.52, 10.33, 10.56, 11.3, 12.12, 13.76, 15.38, 15.87, 19.22, 20.61, 21.55, 22.32, 23.46, 24.89 and 26.26.

15. Form I of 3-[2'-(N-benzoyl)sulfonamidobiphenyl-4-yl]methyl-5,7-dimethyl-2-ethyl-3H-imidazo[4,5-b]pyridine potassium salt as recited in claim 14 which is additionally characterized by a solubility in water of 8.0 mg/mL; a heat of solution in dimethylsulfoxide at 30° C. of about −8.56 J/g; and a heat of solution in 88% dimethylsulfoxide and 12% water of about −25.68 J/g.

16. Form $I_d$ of 3-[2'-(N-benzoyl)sulfonamidobiphenyl-4-yl]methyl-5,7-dimethyl-2-ethyl-3H-imidazo[4,5-b]pyridine potassium salt characterized by about a 1.2% weight loss upon heating from 30° C. to about 150° C. using thermogravimetric analysis.

17. Form $I_d$ of 3-[2'-(N-benzoyl)sulfonamidobiphenyl-4-yl]methyl-5,7-dimethyl-2-ethyl-3H-imidazo[4,5-b]pyridine potassium salt as recited in claim 16 which is additionally characterized by having X-ray powder diffraction angles: 3.62, 7.10, 8.42, 9.98, 11.18, 13.25, 14.56, 16.24, 17.78, 20.43, 22.23, 23.37, 24.79, 29.30, 30.39, 31.25, 31.53, 34.16, and 36.00.

18. Form J of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 3.67, 7.30, 8.53, 10.10, 11.42, 13.33, 14.77, 15.46, 16.32, 17.95, 20.71, 23.76, 23.92, 25.30, and 25.80.

19. Form J of 3-[2'-(N-benzoyl)sulfonamidobiphenyl-4-yl]methyl-5,7-dimethyl-2-ethyl-3H-imidazo[4,5-b]pyridine potassium salt as recited in claim 18 which is additionally characterized by about a 0.7% weight loss upon heating from 30° C. to about 150° C. using thermogravimetric analysis.

20. Form W of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 4.35, 7.46, 8.31, 9.35, 14.91, 18.52, 21.04, 25.35, 28.10, 29.68, 32.98, and 37.34.

21. Form H of 3-[2'-(N-benzoyl)sulfonamidobiphenyl-4-yl]methyl-5,7-dimethyl-2-ethyl-3H-imidazo[4,5-b]pyridine potassium salt characterized by having X-ray powder diffraction angles: 5.78, 6.73, 9.02, 10.41, 11.55, 13.42, 14.33, 15.69, 17.29, 18.36, 20.17, 21.52, 22.47, 23.79, 25.82, 27.80, 28.99, and 30.02.

22. Form H of 3-[2'-(N-benzoyl)sulfonamidobiphenyl-4-yl]methyl-5,7-dimethyl-2-ethyl-3H-imidazo[4,5-b]pyridine potassium salt as recited in claim 21 which is additionally characterized by a differential scanning calorimetric thermogram with a single endotherm at a peak temperature of 259° C.

* * * * *